US010201675B2

(12) United States Patent
Moir et al.

(10) Patent No.: US 10,201,675 B2
(45) Date of Patent: *Feb. 12, 2019

(54) BLOWER AND PAP SYSTEM

(75) Inventors: Michael Bruce Moir, Newbury Park, CA (US); Roman Vinokur, Woodland Hills, CA (US); Frederick Arlet May, Bella Vista (AU); Dmitri Anatolievich Doudkine, Chatswood (AU); Barton John Kenyon, Ashfield (AU); Christopher James Smith, Ingleburn (AU)

(73) Assignee: ResMed Motor Technologies Inc., Chatsworth, CA (US)

(*) Notice: Subject to any disclaimer, the term of this patent is extended or adjusted under 35 U.S.C. 154(b) by 282 days.

This patent is subject to a terminal disclaimer.

(21) Appl. No.: 13/983,712

(22) PCT Filed: Feb. 22, 2012

(86) PCT No.: PCT/AU2012/000175
§ 371 (c)(1),
(2), (4) Date: Aug. 5, 2013

(87) PCT Pub. No.: WO2012/113027
PCT Pub. Date: Aug. 30, 2012

(65) Prior Publication Data
US 2013/0306072 A1 Nov. 21, 2013

Related U.S. Application Data

(60) Provisional application No. 61/446,767, filed on Feb. 25, 2011, provisional application No. 61/457,713, (Continued)

(51) Int. Cl.
A61M 16/00 (2006.01)
A61M 16/06 (2006.01)
(Continued)

(52) U.S. Cl.
CPC .... *A61M 16/0066* (2013.01); *A61M 16/0683* (2013.01); *A61M 16/107* (2014.02);
(Continued)

(58) Field of Classification Search
CPC ............ A61M 16/0066; A61M 16/107; A61M 16/125; A61M 16/0683; A61M 16/0666;
(Continued)

(56) References Cited

U.S. PATENT DOCUMENTS 7,391,140 B2  6/2008  Horng et al.
7,516,743 B2  4/2009  Hoffman
(Continued)

FOREIGN PATENT DOCUMENTS

CN  101296723  10/2008
CN  101324238  12/2008
(Continued)

OTHER PUBLICATIONS

First Examination Report issued in corresponding New Zealand Application No. 706471 dated Apr. 9, 2015.
(Continued)

*Primary Examiner* — Gregory Anderson
*Assistant Examiner* — Elliot S Ruddie
(74) *Attorney, Agent, or Firm* — Nixon & Vanderhye P.C.

(57) ABSTRACT

A blower includes a housing including an inlet and an outlet, a stationary component provided to the housing, an impeller positioned between the inlet of the housing and the stationary component, and a motor adapted to drive the impeller. The stationary component includes a tube portion structured to retain and align a pair of bearings that rotatably support a rotor to which the impeller is coupled. The tube portion includes a diameter in a side closest to the impeller that is sufficient size to accommodate adhesive to retain one of the bearings.

20 Claims, 38 Drawing Sheets

Related U.S. Application Data filed on May 18, 2011, provisional application No. 61/573,131, filed on Sep. 9, 2011.

(51) Int. Cl.

| | | |
|---|---|---|
| *F04D 17/16* | (2006.01) | |
| *F04D 29/048* | (2006.01) | |
| *F04D 17/08* | (2006.01) | |
| *A61M 16/10* | (2006.01) | |
| *A61M 16/12* | (2006.01) | |

(52) U.S. Cl.
CPC ........... *A61M 16/125* (2014.02); *F04D 17/08* (2013.01); *F04D 17/16* (2013.01); *F04D 29/048* (2013.01); *A61M 16/0666* (2013.01); *A61M 2202/0208* (2013.01); *A61M 2205/3358* (2013.01); *A61M 2205/42* (2013.01)

(58) Field of Classification Search
CPC .. A61M 2202/0208; A61M 2205/3358; A61M 2205/42; A61M 16/0057; A61M 16/0875; F04D 17/08; F04D 17/16; F04D 29/048; F04D 25/0606; F04D 29/601; F04D 29/668; F04D 25/062; F04D 29/444; F04D 29/059
USPC ............ 128/204.18, 204.21, 204.23, 205.25, 128/203.24; 310/90; 417/423.14
See application file for complete search history.

(56) References Cited

U.S. PATENT DOCUMENTS

| | | | |
|---|---|---|---|
| 7,789,194 B2 | 9/2010 | Lathrop et al. | |
| 7,866,944 B2 | 1/2011 | Kenyon et al. | |
| 8,973,576 B2 * | 3/2015 | Kenyon | A61M 16/0066 128/204.18 |
| 2005/0052089 A1 | 3/2005 | Horng et al. | |
| 2006/0237013 A1 | 10/2006 | Kwok | |
| 2007/0075598 A1 | 4/2007 | Tung et al. | |
| 2007/0210660 A1 | 9/2007 | Horng et al. | |
| 2007/0247009 A1 | 10/2007 | Hoffman et al. | |
| 2008/0218018 A1 | 9/2008 | Zhang et al. | |
| 2008/0304986 A1 * | 12/2008 | Kenyon | H02K 5/128 417/423.12 |
| 2009/0007912 A1 | 1/2009 | Lindell et al. | |
| 2009/0056715 A1 * | 3/2009 | Cortez, Jr. | A61M 16/08 128/203.26 |
| 2009/0136341 A1 | 5/2009 | Kenyon | |
| 2009/0246013 A1 | 10/2009 | Kenyon et al. | |
| 2009/0320842 A1 | 12/2009 | Doherty et al. | |
| 2010/0132711 A1 | 6/2010 | Kenyon | |
| 2010/0229868 A1 * | 9/2010 | Rummery | A61M 16/06 128/205.25 |
| 2010/0329901 A1 | 12/2010 | Horng | |
| 2011/0073110 A1 | 3/2011 | Kenyon et al. | |
| 2012/0138058 A1 * | 6/2012 | Fu | A61M 16/0066 128/204.23 |
| 2012/0152255 A1 | 6/2012 | Barlow et al. | |
| 2012/0199129 A1 * | 8/2012 | Kenyon | A61M 16/0066 128/205.25 |

FOREIGN PATENT DOCUMENTS

| | | | |
|---|---|---|---|
| CN | 101328910 | 12/2008 | |
| EP | 2 000 675 | 12/2008 | |
| GB | 2 435 905 B | 2/2008 | |
| JP | S63-51498 | 4/1988 | |
| JP | 2004-135416 A | 4/2004 | |
| JP | 2004135416 A * | 4/2004 | |
| JP | 2009-533153 | 9/2009 | |
| WO | WO 2004/108198 | 12/2004 | |
| WO | WO 2007/024955 | 3/2007 | |
| WO | WO 2007/048205 | 5/2007 | |
| WO | WO 2007/048206 | 5/2007 | |
| WO | 2008/051534 A2 | 5/2008 | |
| WO | WO 2010139014 A1 * | 12/2010 | ............ A61M 16/06 |
| WO | WO 2011/006206 | 1/2011 | |
| WO | WO 2011/017763 | 2/2011 | |
| WO | WO 2011/022779 | 3/2011 | |
| WO | WO 2011/062633 | 5/2011 | |
| WO | WO 2011062633 A1 * | 5/2011 | ........ A61M 16/0066 |
| WO | WO 2007/134405 | 11/2011 | |

OTHER PUBLICATIONS

First Office Action issued in corresponding Chinese Application No. 201280010544.5 dated Apr. 21, 2015, with English translation thereof.
First Examination Report issued in corresponding New Zealand Appln. No. 614063 dated Jun. 26, 2014.
Patent Examination Report issued in corresponding Australian Appln. No. 2012220358 dated Jun. 30, 2014.
International Search Report issued in PCT Appl. No. PCT/AU2012/000175 (dated Jun. 26, 2012).
Patent Examination Report No. 2 issued in corresponding Australian Appln. No. 2012220358, dated Oct. 13, 2014.
Extended European Search Report issued in corresponding European Appln. No. 12 74 9644.6 dated Jan. 7, 2016.
Second Office Action issued in corresponding Chinese Application No. 201280010544.5 dated Dec. 10, 2015 with English translation thereof.
International Preliminary Report on Patentability issued in corresponding PCT Application No. PCT/AU2012/000175 dated Jan. 23, 2013.
Patent Examination Report No. 1 issued in corresponding Australian Application No. 2015200468 dated Dec. 1, 2015.
Further Examination Report issued in a corresponding New Zealand Application No. 706471 dated Mar. 16, 2016.
Notice of Reasons for Rejection dated Oct. 31, 2016 issued in Japanese Application No. 2013-554750 with English translation (8 pages).
First Examination Report dated Oct. 12, 2016 issued in New Zealand Application No. 724102 (3 pages).
Communication dated Mar. 8, 2017 issued in New Zealand Application No. 706471 (1 page).
Notice of Opposition to Grant of Patent (Section 21) filed Feb. 28, 2017 by Fisher & Paykel Healthcare Limited in New Zealand Application No. 706471 (2 pages).
Communication Regarding Deadline for Counterstatement dated May 18, 2017 issued in New Zealand Application No. 706471 (2 pages).
Second Amended Notice of Opposition to Grant of Patent (Section 21), with no markups, dated Apr. 28, 2017, filed by Fisher & Paykel Healthcare Limited in New Zealand Application No. 706471 (2 pages).
Second Amended Notice of Opposition to Grant of Patent (Section 21), with markups, dated Apr. 28, 2017, filed by Fisher & Paykel Healthcare Limited in New Zealand Application No. 706471 (2 pages).
Statement of Case dated Apr. 28, 2017, filed by Fisher & Paykel Healthcare Limited in New Zealand Application No. 706471 (13 pages).
Decision of Rejection dated Jun. 19, 2017 issued in Japanese Application No. 2013-554750 with English translation (7 pages).
Communication dated Mar. 29, 2018 issued in European Application No. 12749644.6 (18 pages).
First Examination Report dated May 3, 2018 issued in New Zealand Application No. 741288 (3 pages).
First Office Action issued in corresponding Japanese Application No. 2013-554750 dated Feb. 8, 2016, with English translation thereof.

* cited by examiner

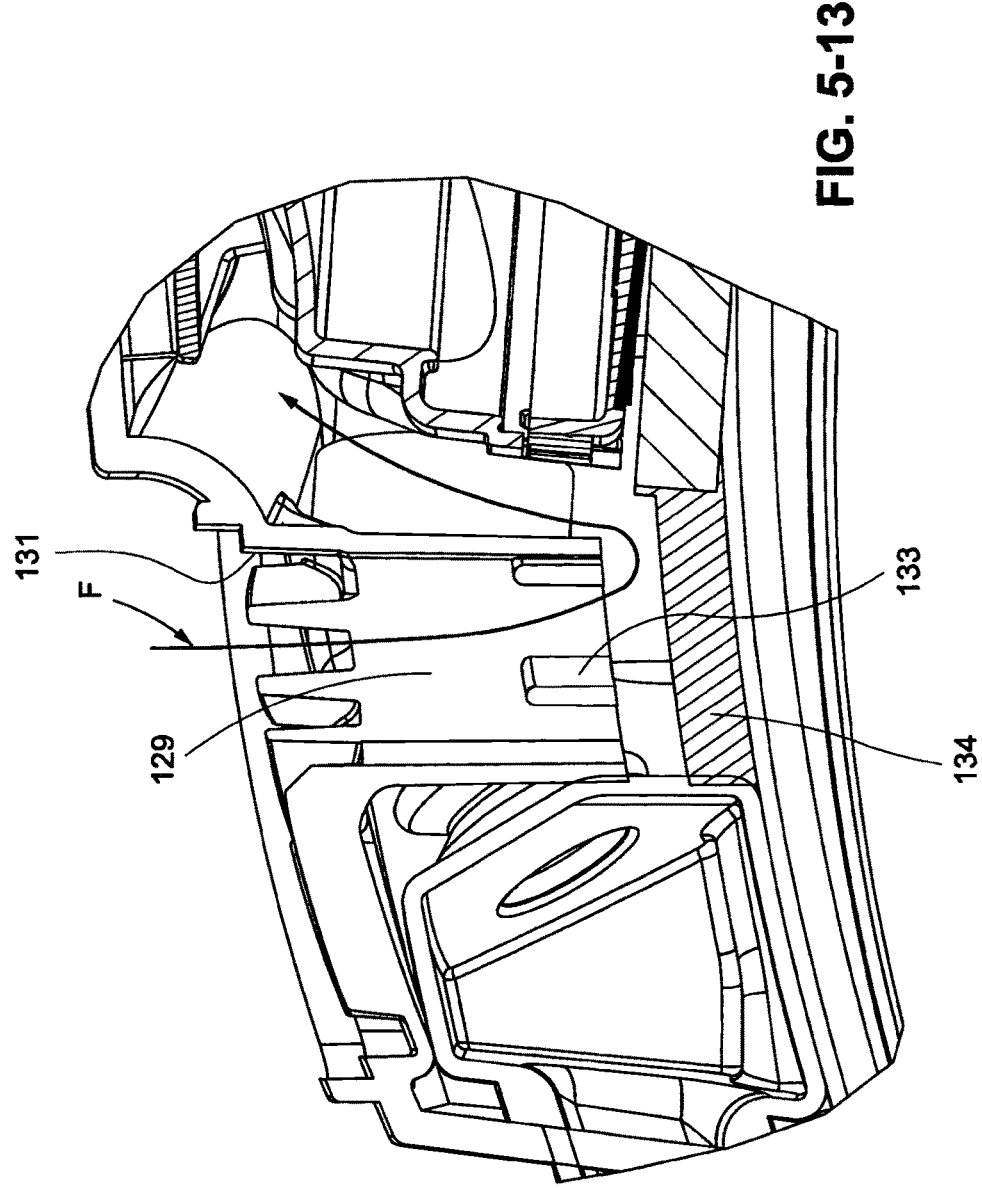

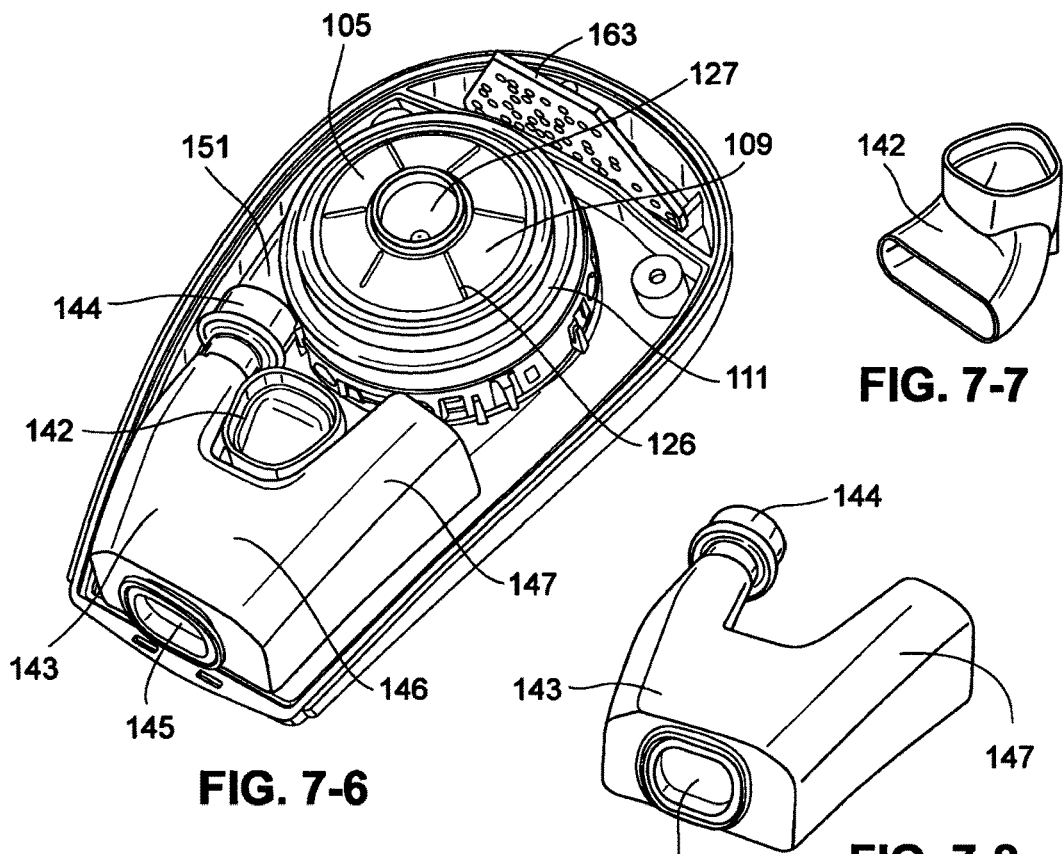
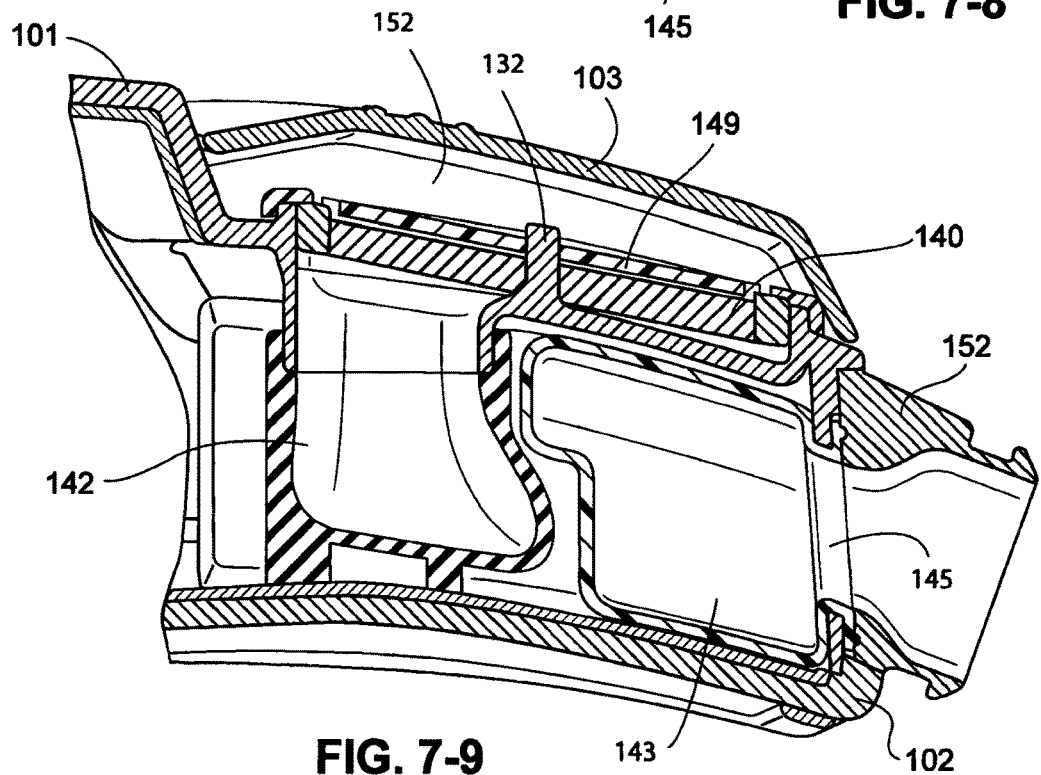

BLOWER AND PAP SYSTEM

CROSS-REFERENCE TO RELATED APPLICATIONS

This application is the U.S. national phase of International Application No. PCT/AU2012/000175 filed 22 Feb. 2012 which designated the U.S. and claims priority to U.S. Provisional Application No. 61/446,767 filed 25 Feb. 2011, U.S. Provisional Application No. 61/457,713 filed 18 May 2011, and U.S. Provisional Application No. 61/573,131 filed 9 Sep. 2011, the entire contents of each of which are hereby incorporated by reference.

Also, International Application No. PCT/AU2010/001106, filed Aug. 27, 2010, is incorporated herein by reference in its entirety. International Application No. PCT/AU2010/001106 claims the benefit of U.S. Provisional Application Nos. 61/272,188, filed Aug. 28, 2009, and 61/272,919, filed 19 Nov. 2009, and Australian Provisional Application Nos. AU 2010900237, filed 22 Jan. 2010, 2010900304, filed 27 Jan. 2010, 2010900455, filed 5 Feb. 2010, and 2010900647, filed 18 Feb. 2010, the entire contents of each being incorporated herein by reference.

Also, U.S. Provisional Application Nos. 61/213,326, filed May 29, 2009, 61/222,711, filed Jul. 2, 2009, 61/272,043, filed Aug. 11, 2009, 61/272,162, filed Aug. 25, 2009, 61/272,250, filed Sep. 4, 2009, and 61/344,588, filed Aug. 27, 2010, are each incorporated herein by reference in their entirety. International Application No. PCT/AU2010/001031, filed Aug. 11, 2010, and International Application No. PCT/US2010/003010, filed Nov. 19, 2010, are each incorporated herein by reference in their entirety.

FIELD OF TECHNOLOGY

The present technology relates to a blower for generating a pressure differential and Positive Airway Pressure (PAP) systems and/or methods of use for treatment, e.g., of Sleep Disordered Breathing (SDB) with Continuous Positive Airway Pressure (CPAP) or Non-Invasive Positive Pressure Ventilation (NIPPY). In an example, the blower may be used in a PAP device used for the delivery of respiratory therapy to a patient. Examples of such therapies are Continuous Positive Airway Pressure (CPAP) treatment, Non-Invasive Positive Pressure Ventilation (NIPPY), and Variable Positive Airway Pressure (VPAP). The therapy is used for treatment of various respiratory conditions including Sleep Disordered Breathing (SDB) and more particularly Obstructive Sleep Apnea (OSA). However, the blower and PAP systems may be used in other applications (e.g., vacuum applications (medical or otherwise)).

BACKGROUND OF TECHNOLOGY

A need has developed in the art for blower designs that are quieter and more compact. The present technology provides alternative arrangements of blowers that consider this need. Examples of head mounted blowers, wearable CPAP, or portable CPAP are known in the art. For example, see U.S. Patent Application Publications 2006/0237013 A1 and 2009/0320842 A1, each incorporated herein by reference, and the BreatheX™ system.

SUMMARY OF TECHNOLOGY

An aspect of the disclosed technology relates to minimalistic CPAP systems, methods of use and devices structured to at least reduce impact on the patient.

Another aspect of the disclosed technology relates to CPAP systems, methods of use and devices structured to at least reduce size and bulk, reduce vibrations, reduce generated noise or combinations thereof.

Another aspect relates to small CPAP devices configured to supply pressurized breathable gas (e.g., air) in a manner suitable for treatment of sleep apneas.

Another aspect of the disclosed technology relates to improvements and/or alternative examples of the blower described in PCT Application No. PCT/US2010/003010, e.g., to mitigate blower noise.

Another aspect of the disclosed technology relates to a stationary component structured to accommodate adhesive for retaining a bearing that rotatably supports a shaft of a blower, e.g., to reduce acoustic tonal peaks.

Another aspect of the disclosed technology relates to a rotor or shaft of a blower that includes at least one annular groove, e.g., to reduce shaft stiffness and increase loss factor in order to attenuate the rotor mechanical resonances, lower the magnitude of the imbalance, and/or reduce bearing frequency peaks in the blower narrow band acoustics in use.

In an example, the rotor is supported by a pair of bearings, and the at least one groove is adapted to be positioned between the bearings.

In an example, the at least one groove has a diameter between about 50% and about 95% of the outer diameter of the rotor.

In an example, the at least one groove has a width that is between about 20% and about 50% of the outer diameter of the rotor.

In an example, the rotor may include a plurality of smaller grooves along the length of the rotor, e.g., the plurality of smaller grooves arranged on a double helix configuration, to enhance retention of an impeller.

In an example, the rotor may include a smaller annular groove adapted to receive a retaining ring structured to maintain the rotor within the blower, e.g., retain the rotor within a tube portion adapted to receive a pair of bearings and the rotor.

Another aspect of the disclosed technology relates to a stationary assembly of a blower that includes a plurality of mounting protrusions, e.g., 3 or more mounting protrusions, to precisely position and align a printed circuit board assembly (PCBA) and its attendant components accurately with respect to the stationary assembly.

Another aspect of the disclosed technology relates to a housing part of a blower that includes a chimney or inlet tube portion, e.g., constructed of TPE and overmolded to the housing part, made for the turbulent noise reduction with no significant restriction to the air flow provided to the inlet of the housing part.

Another aspect of the disclosed technology relates to a blower bracket to locate and align a blower within a casing including a removable cover.

Another aspect of the disclosed technology relates to an inlet elbow of a flow generator structured to direct air flow from an air inlet opening provided to an upper housing of the housing to a lower housing of the housing.

In an example, a lower end of inlet elbow terminates above the lower housing with a gap.

In an example, air flow is dispersed in all directions, e.g., 360°, into the internal area of the housing upon exiting the lower end of the inlet elbow.

In an example, the inlet elbow may have a curved shape that may reflect back sound wavelengths to further reduce noise generated by the blower.

Another aspect of the disclosed technology relates to a blower including a housing including an inlet and an outlet, a stationary component provided to the housing, an impeller positioned between the inlet of the housing and the stationary component, and a motor adapted to drive the impeller. The stationary component includes a tube portion structured to retain and align a pair of bearings that rotatably support a rotor to which the impeller is coupled. The tube portion includes a diameter in a side closest to the impeller that is sufficient size to accommodate adhesive to retain one of the bearings.

Another aspect of the disclosed technology relates to a blower including a housing including an inlet and an outlet, a stationary component provided to the housing, an impeller positioned between the inlet of the housing and the stationary component, and a motor adapted to drive the impeller. The motor includes a rotor to which the impeller is coupled, the rotor including at least one annular groove, e.g., positioned between a pair of bearings or along a length of the rotor that is adjacent the bearings.

Another aspect of the disclosed technology relates to a PAP device including a casing, a blower provided within the casing, and a blower bracket to locate and align the blower within the casing.

Another aspect of the disclosed technology relates to a blower including a housing including an inlet and an outlet, a stationary component provided to the housing, an impeller positioned between the inlet of the housing and the stationary component, and a motor adapted to drive the impeller. The motor includes a rotor coupled to the impeller. At least two of the following noise reduction features are provided in the blower: (i) the stationary component includes a tube portion structured to retain and align a pair of bearings that rotatably support the rotor, the tube portion including a diameter in a side closest to the impeller that is sufficient size to accommodate adhesive to retain one of the bearings; (ii) the rotor includes at least one annular groove; (iii) the stationary component and a stator assembly of the motor are overmolded with one another to provide a stationary assembly, the stationary assembly including a plurality of mounting protrusions to precisely position and align a printed circuit board assembly and its attendant components accurately with respect to the stationary assembly, and at least one of the protrusions is positioned near a Hall sensor of the printed circuit board assembly; (iv) a blower bracket to locate and align the blower within a casing; and/or (v) a chimney or inlet tube portion provided to the inlet of the housing.

Another aspect of the disclosed technology relates to a blower including a housing including an inlet and an outlet, a stationary component provided to the housing, an impeller positioned between the inlet of the housing and the stationary component, and a motor adapted to drive the impeller. The stationary component and a stator assembly of the motor are overmolded with one another to provide a stationary assembly. The stationary assembly includes a plurality of mounting protrusions to precisely position and align a printed circuit board assembly and its attendant components accurately with respect to the stationary assembly. At least one of the protrusions is positioned near a Hall sensor of the printed circuit board assembly.

Another aspect of the disclosed technology relates to a flow generator adapted to provide a supply of pressurized breathable gas for treatment of a respiratory disease or sleep disordered breathing. The flow generator includes: a housing, the housing including an upper housing and a lower housing sealingly connected together, the upper housing including an air inlet opening; an inlet elbow in fluid communication with the air inlet opening; and a blower. The blower includes a blower housing including an inlet and an outlet, a stationary component provided to the blower housing, an impeller positioned between the inlet of the blower housing and the stationary component, and a motor adapted to drive the impeller, the motor including a rotor coupled to the impeller. The inlet elbow is adapted to direct air flow from the air inlet opening to the lower housing.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 4-1 to 4-4 show exploded views of a connector tube and a short outlet tube according to an example of the disclosed technology;

FIGS. 5-1 to 5-13 show a PAP device, or flow generator assembly, according to an example of the disclosed technology;

FIGS. 6-1 and 6-2 show a PAP device, or flow generator assembly, according to an example of the disclosed technology;

FIGS. 7-1 to 7-12 show a PAP device, or flow generator assembly, according to an example of the disclosed technology;

FIGS. 8 and 9 show PAP devices, or flow generator assemblies, according to examples of the disclosed technology;

FIG. 10 shows a flow generator device according to an example of the disclosed technology;

FIG. 11 shows a flow generator device according to an example of the disclosed technology;

FIG. 12 is a cross-sectional view of a blower according to an example of the disclosed technology;

FIG. 13 is an enlarged cross-sectional view showing a tube portion of a blower according to an example of the disclosed technology;

DETAILED DESCRIPTION OF ILLUSTRATED EXAMPLES

Figure 1:
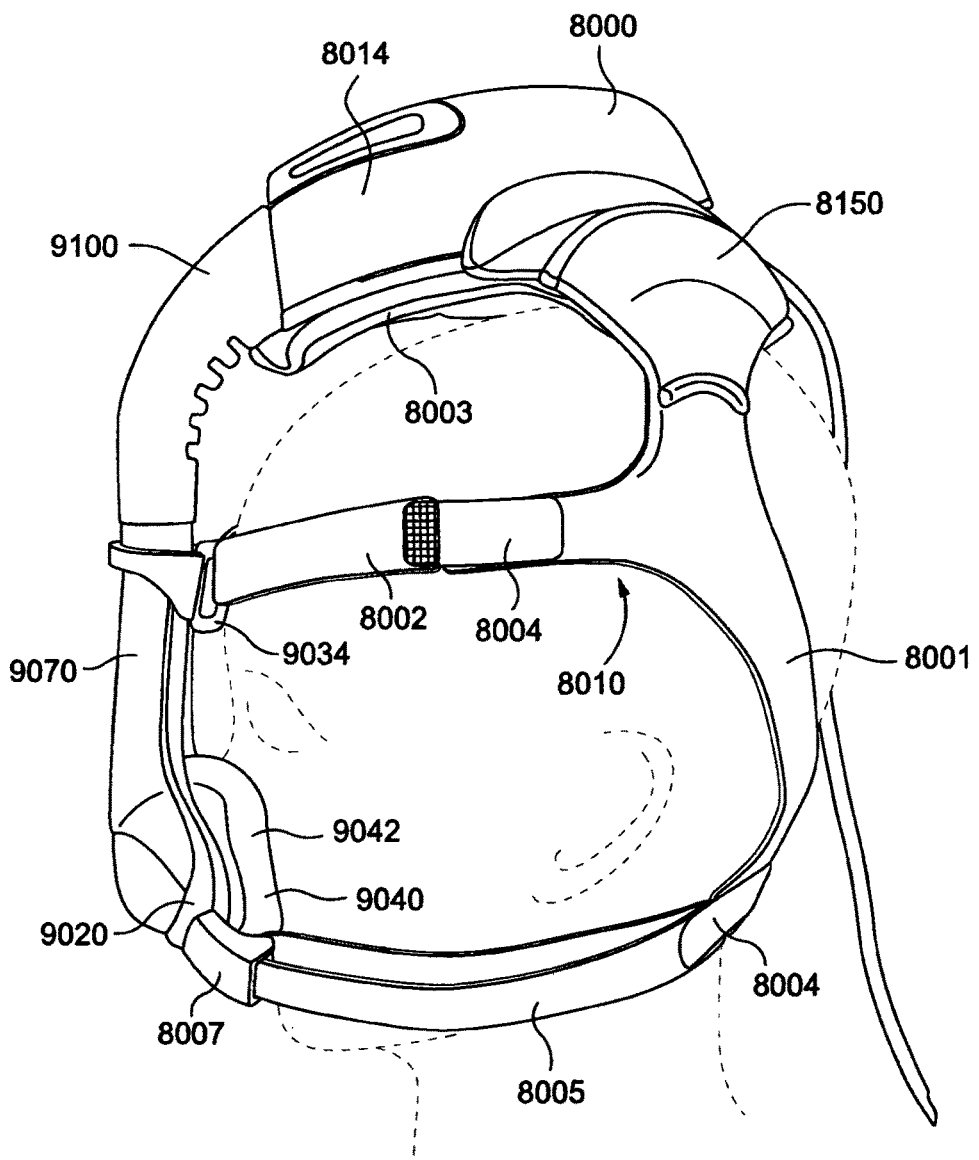
FIG. 1 is a side view of a PAP system according to an example of the disclosed technology.

The following description is provided in relation to several examples (some of which are illustrated, some of which may not) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Aspects of the technology will be described herein in its application to non-invasive ventilation (NIVV) treatment apparatus (e.g., positive airway pressure (PAP) devices), such as CPAP, but it is to be understood that aspects of the technology may have application to other fields of application where blowers are used, e.g., in both positive pressure and negative pressure applications.

In this specification, the words "air pump" and "blower" may be used interchangeably. The term "air" may be taken to include breathable gases, for example air with supplemental oxygen. It is also acknowledged that the blowers described herein may be designed to pump fluids other than air.

Also, each blower example below is described as including a single stage design. However, it should be appreciated that examples of the technology may be applied to multiple stage designs, e.g., two, three, four, or more stages.

Further examples of blowers and aspects related to the present technology are disclosed in PCT Application No. PCT/US2010/003010, filed Nov. 19, 2010, which is incorporated herein by reference in its entirety.

Each illustrated example includes one or more features that may be adapted for use and/or incorporated into examples and/or components of the blower described in PCT Application No. PCT/US2010/003010, as would be apparent to those of ordinary skill in the art.

While each illustrated example is described as being implemented into a blower of the type described in PCT Application No. PCT/US2010/003010, each illustrated example may be implemented into other blowers.

Exemplary PAP Systems and Blowers

A PAP system (e.g., CPAP system) typically includes a PAP device (including a blower for generating air at positive pressure), an air delivery conduit (also referred to as a tube or tubing), and a patient interface. In use, the PAP device generates a supply of pressurized air (e.g., 2-30 cmH$_2$O, typically around 8-12 cmH$_2$O) that is delivered to the patient interface via the air delivery conduit. The patient interface or mask may have suitable configurations as is known in the art, e.g., full-face mask, nasal mask, oro-nasal mask, mouth mask, nozzles, nasal prongs, etc. Also, headgear may be utilized to comfortably support the patient interface in a desired position on the patient's face.

Certain examples relate to PAP systems in which the PAP device or blower is adapted to be worn on the patient's head, is built into or incorporated into the patient interface or mask, is wearable or carried by the patient, is portable, is reduced in size or combinations thereof. In certain examples, the PAP device may be of the type described in PCT Application No. PCT/US2010/001106, which is incorporated herein by reference in its entirety. The following examples include improvements and/or alternatives to this PAP device, e.g., to mitigate device noise. In certain examples, the blower may be of the type described in PCT Application No. PCT/US2010/003010, which is incorporated herein by reference in its entirety. The following examples include improvements and/or alternatives to this blower, e.g., to mitigate blower noise.

PAP System Example

Figure 2:
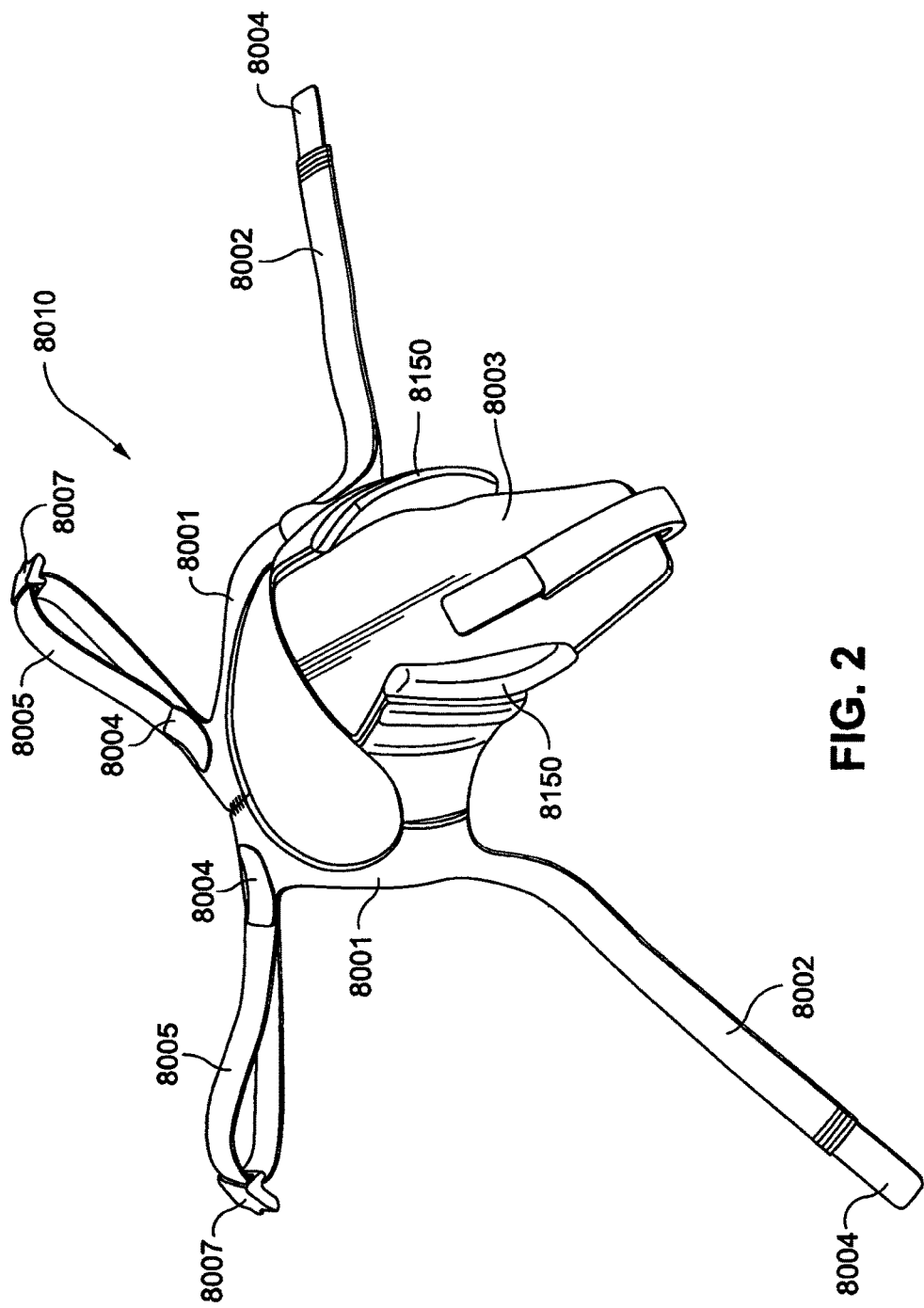
FIG. 2 is a perspective view of headgear of the PAP system of FIG. 1.
Figure 3:
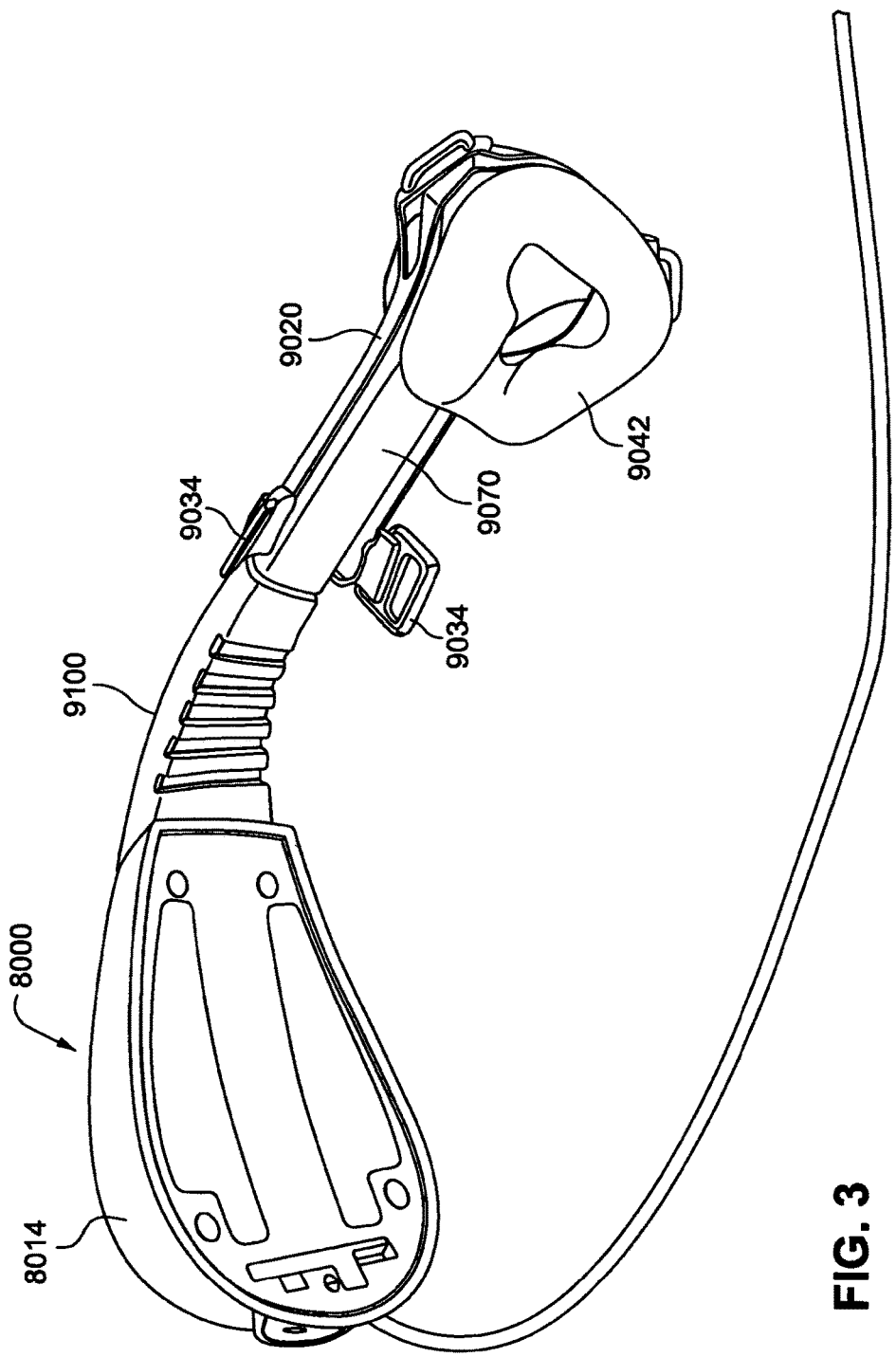
FIG. 3 is a perspective view of a PAP device of the PAP system of FIG. 1.

FIGS. 1-3 illustrate an example of a headworn PAP system comprising a PAP device 8000 that includes a blower or flow generator as described in International application PCT/AU2010/001106. Referring to FIG. 1, the PAP device 8000 is supported on an extension 8003 of a headgear 8010 and is secured between two raised portions 8150 that extend from the extension 8003 of the headgear. Upper headgear straps 8002 are connected to upper headgear connectors 9034 of a frame 9020 of a patient interface system that supports a patient interface device, or cushion, 9042 in sealing engagement with the face of the patient. The upper headgear straps 8002 are connected to the headgear by fasteners 8004.

Lower headgear straps 8005 are connected to the frame 9020 by headgear connector clips 8007 that attach to the frame 9020. As shown in FIG. 1, the lower headgear straps 8005 are connected to the occipital ring 8001 of the headgear at the back of the patient's head by fasteners 8004. The fasteners 8004 for the upper headgear straps 8002 and the lower headgear straps 8005 may be, for example, hook and loop fasteners, such as Velcro™.

The extension 8003 may be shaped to cover the entire lower surface of the flow generator 8014, when the flow generator is mounted. The extension portion 8003 may include an electromagnetic force (EMF) shield adapted to be inserted or encapsulated within the headgear. The EMF shield may comprise a relatively small piece of sheet metal generally cut into a shape to match the flow generator footprint with a rounded bottom and rounded corners. However, the EMF shield may be made in other shapes. The EMF shield may be positioned between the motor and electronics of the flow generator 8014 and the patient's head, this may prevent, limit or mitigate the potential for EMF or ionising radiation adversely affecting the patient, when using the PAP device for extended periods of time, or during repeated uses. The EMF shield may also assist in reducing noise as the additional mass of the EMF shield would reduce vibrations.

The patient interface system, which may be, for example, a nasal mask system or a full face mask system comprises the frame 9020 which supports the sealing arrangement 9040. The sealing arrangement 9040 comprises the cushion 9042 which is configured to sealingly engage the face of the patient.

The flow generator may deliver pressurized breathable gas to the patient interface system by a relatively short length of tubing 9100, also referred to as an intermediate tube or connector tube or outlet tube. The outlet tube is adapted to couple to the inlet tube 9070 of the patient interface system.

Connector Tube and Outlet Tube Example

Figures 1, 4:
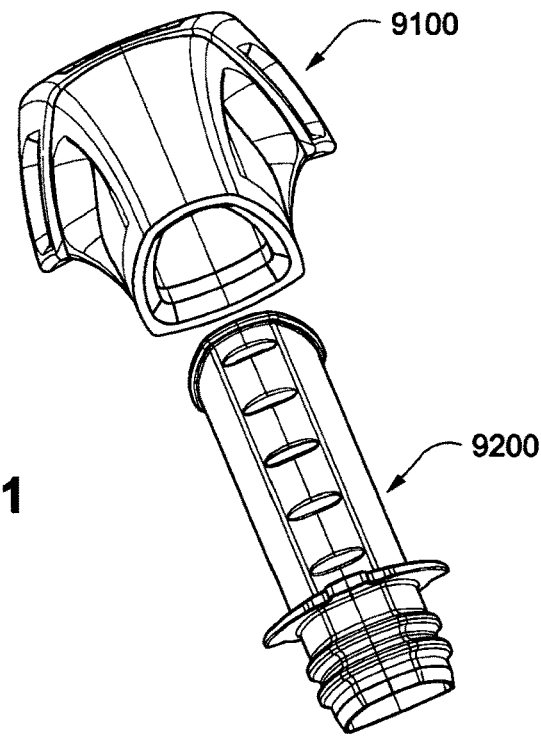
Figures 2, 4:
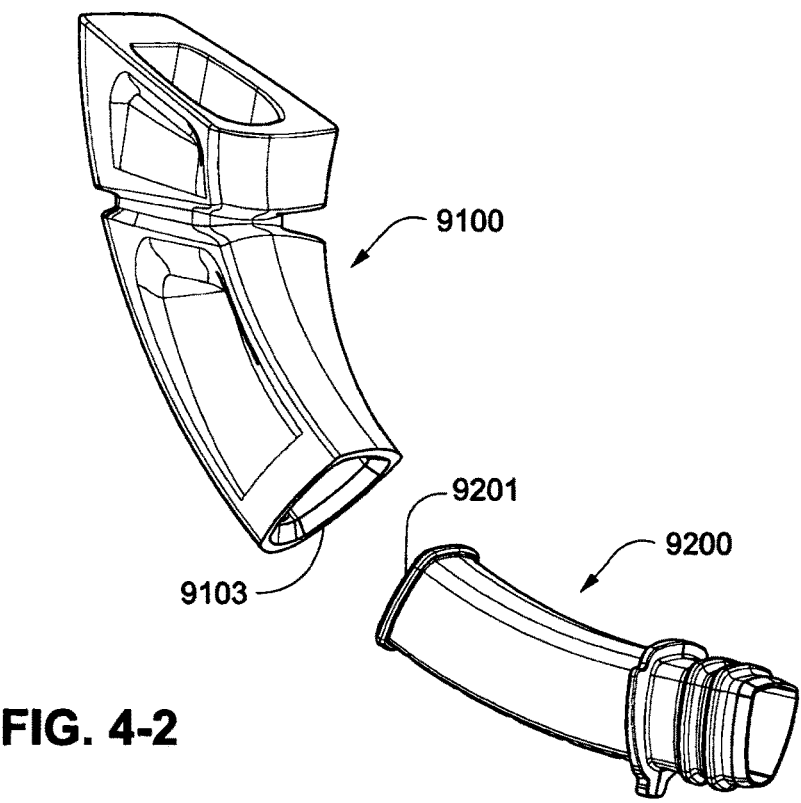
Figures 3, 4:
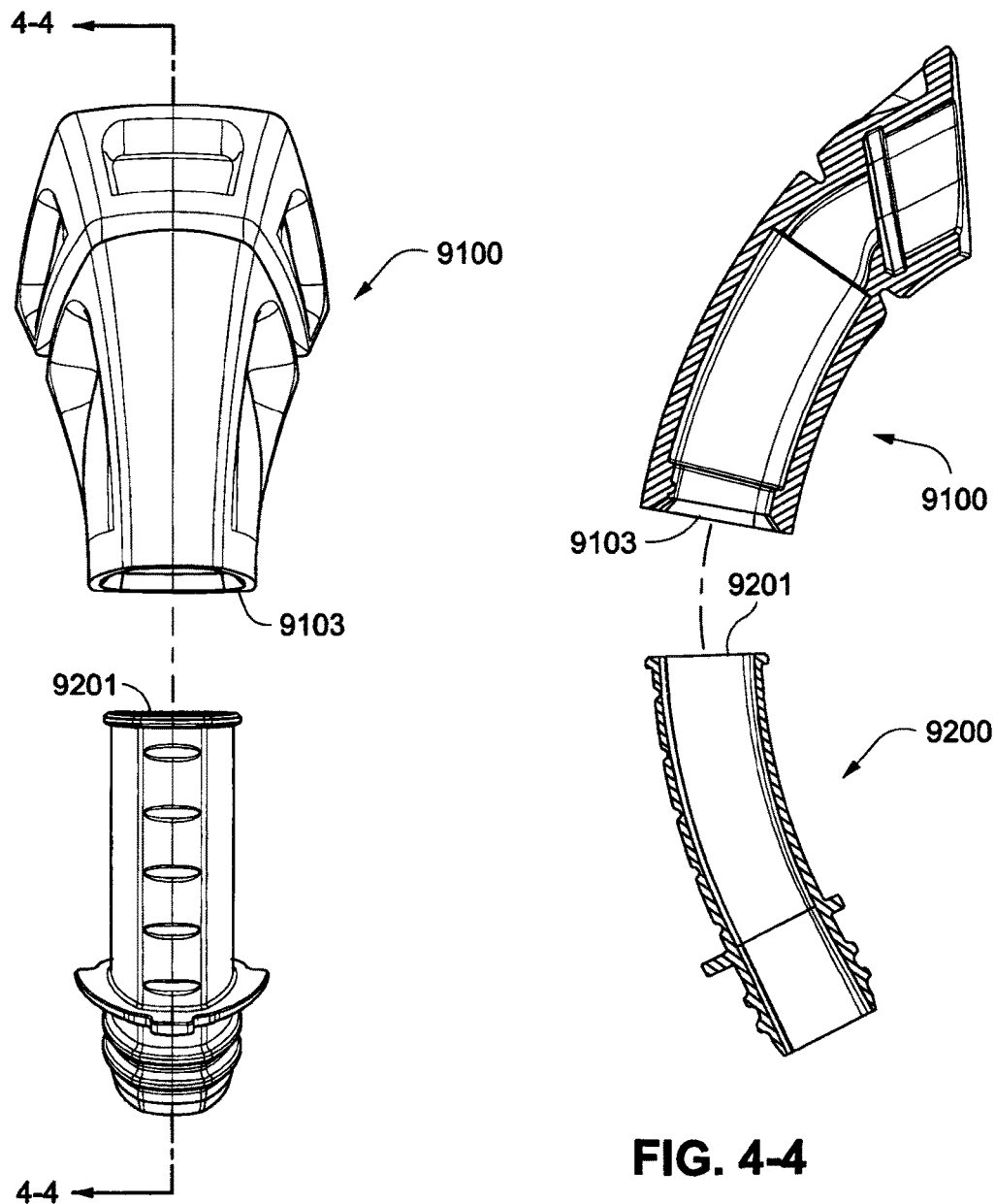

In an alternative arrangement, as shown in FIGS. 4-1 to 4-4, the patient interface system may include a connector tube 9200 having a first end 9201 configured to be attached to a short outlet tube 9100 that is configured to be connected to the PAP device. The first end 9201 of the connector tube 9200 is configured to be inserted into a second end 9103 of the short outlet tube 9100.

The short outlet tube 9100, or the short outlet tube 9100 in combination with the connector tube 9200 between the flow generator and the patient interface (e.g., mask), reduces the resistance and impedance of the air flow. The entire air path from the outlet of the blower to the patient interface may be designed such that the volume of the air flow is expanding and contracting repeatedly and ultimately is expanded into the patient interface. The repeated expansion and contraction and ultimate expansion into the patent interface slows down the air flow and increases the pressure. The air flow path may be provided with smooth, gradual transitions which will allow more choke within the blower, for example at the inlet which reduces the inlet noise, and which provide more resistance within the flow generator which also reduces noise.

PAP Device Example

Referring to FIGS. 5-1 to 5-13, a PAP device 100 according to certain examples is illustrated. The PAP device 100 comprises an upper housing 101 and a lower housing 102 that form a housing for a blower, or flow generator, 105 that is configured to generate a flow of pressurized breathable gas. A filter cover 103 is provided on the upper housing 101 to cover a filter which may be replaceably provided in the upper housing 101. The filter cover 103 covers the filter inlet 131 on the housing for a blower, or flow generator, 105. The filter inlet 131 supports filter material such that the edges of the filter material remain in position. The filter cover 103 also includes retention features or ribs adapted to prevent collapse of the filter during air flow therethrough. Airflow F enters in the inlet 131 through air inlet clearances, or openings, 152 in the upper housing 101 and down through an inlet tube 129 that directs air vertically downwards towards the lower housing 102. The inlet tube 129 may have a cross-sectional area of approximately 150 mm$^2$ to approximately 300 mm$^2$, or approximately 150 mm$^2$ to approximately 250 mm$^2$ or approximately 200 mm$^2$. The inlet tube 129 has a vertical opening transversing from the filter inlet 131 towards the lower housing 102. The lower end of the inlet tube 129 terminates above the lower housing 102 with a gap such as a 10-18 mm gap, for example a 13-15 mm gap, to allow air flow out of the lower end of the inlet tube 129 and into the internal area of the housing 101, 102. The inlet tube 129 increases the path length at the inlet 127 to the blower 105, as shown in FIGS. 5-12 and 5-13. The inlet tube 129 may be formed of a soft material, for example silicone, to allow movement of the walls of the inlet tube 129. The inlet tube 129 also prevents finger ingress to the inlet 127 of the blower 105. The inlet tube 129 acts as a muffler as the larger the mass of air present within the inlet, the less it is able to vibrate, thus attenuating the noise within the PAP device 100.

The inlet tube 129 may comprise two vanes 133 at the lower end of the inlet tube 129 to prevent foreign objects from being trapped within the inlet tube 129 and blocking the inlet tube 129 (e.g., see FIGS. 5-11 and 5-13). It should be appreciated that one or more vanes or other structures may be used to prevent blockage of the inlet tube 129. Once the air exits the lower end of the inlet tube it is dispersed in all directions, or 360°, into the internal area of the housing and travels up to the inlet 127 of the blower 105. The rotation of the impeller 112 of the blower 105 will assist in drawing the incoming air towards the inlet 127. In a certain example, a noise absorbing material 134 such as foam, for example Accusorb™ foam, is attached to the lower housing 102 below the inlet tube 129 to assist in reducing or muffling the noise generated from the inlet 131. The foam 134 may have a thickness of about 3-8 mm, such as 4-6 mm, such as 4.5 mm. It should be appreciated that other thicknesses of foam may be used depending upon the size of the housing. In operation the inlet air flow is directed through the filter inlet 131, down the inlet tube 129 and into contact with the foam 134 below the inlet tube 129 and is dispersed throughout the internal cavity of the housing 101, 102. The direction and air flow path of the filter inlet 131 and inlet tube 129 reduce the noise level transmitted from the inlet 131.

Figures 1, 5:
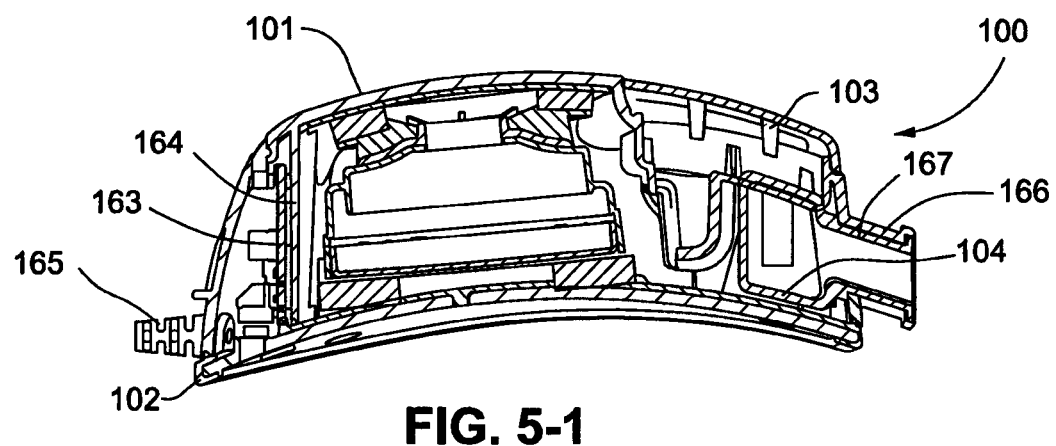
Figures 2, 5:
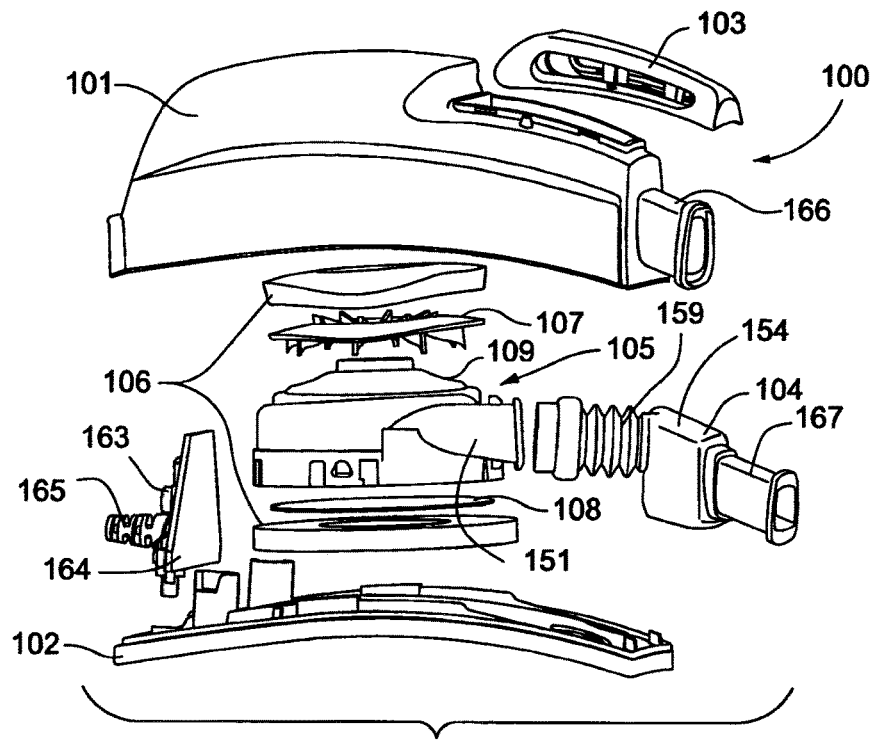
Figures 3, 5:
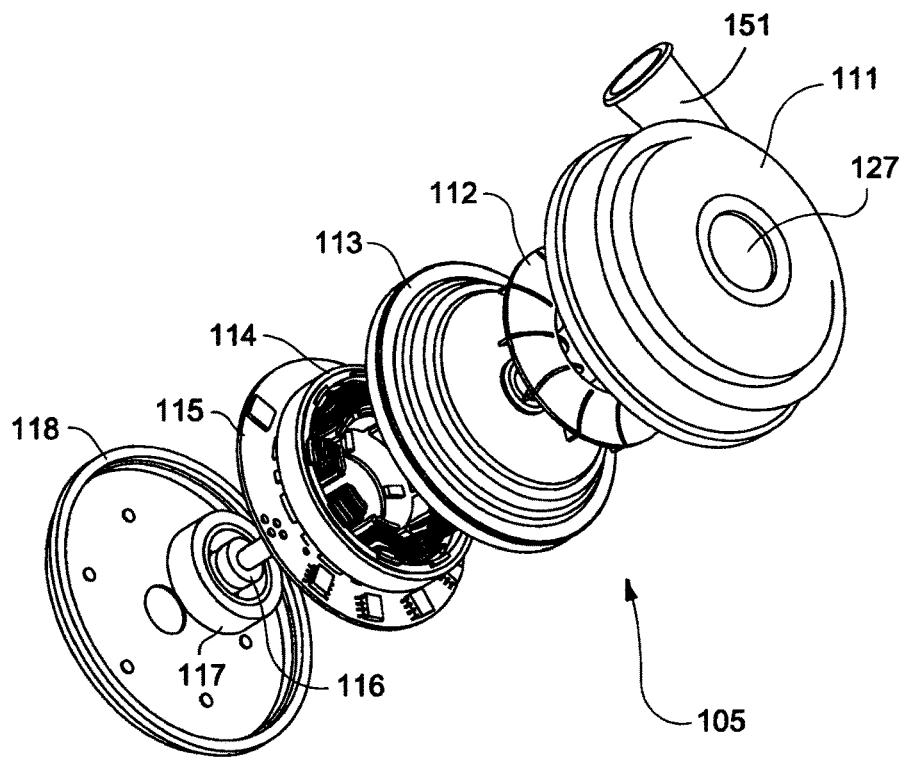
Figures 4, 5:
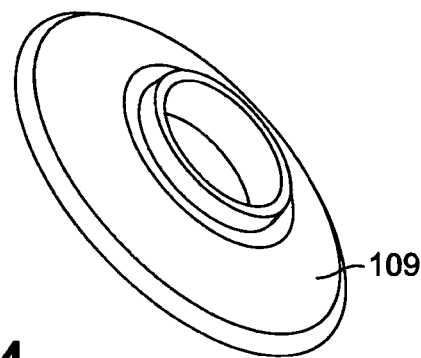
Figure 5:
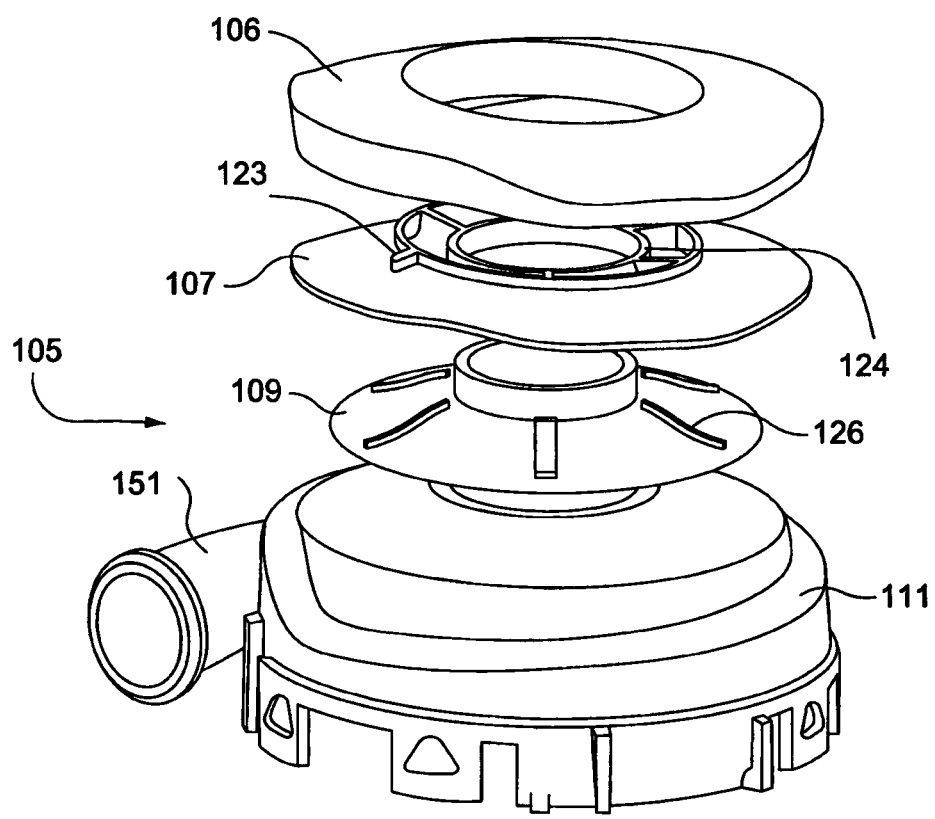

Referring to FIG. 5-2, the blower 105 is provided in the housing between foam supports 106. An air inlet guide, or chimney, 109 may be provided to the blower 105. For example, the chimney 109 may be overmolded onto the blower 105. An inlet cage 107 is provided between the foam support 106 and the chimney 109 to support the upper foam support 106 in a fixed position above the blower 105 and establish a fixed inlet path to the blower chimney 109.

As shown in FIGS. 5-1 and 5-2, an outlet tube 154 having a muffler chamber 104 is connected to the outlet 151 of the blower 105 to reduce the noise of the airflow generated by the blower 105. The outlet tube 154 may further include a bellows 159. The outlet tube 154 may be made of a flexible or elastomeric material, for example, silicone. The outlet tube 154 includes an outlet 167 that extends through an outlet 166 of the upper housing 101.

The foam supports 106 may be provided above and below the blower 105. The majority of the vibration of the blower 105 is on one axis, from side to side. The blower 105 may be arranged such that it allows movement from side to side without touching, or substantially touching, structural features in the housing of the PAP device and so that the blower 105 is surrounded by air. The wires have been decoupled from the blower 105.

Vibration is absorbed for vibrations in the opposing axis, i.e. up and down. The foam supports 106 are placed on the top and bottom of the blower 105. The foam supports 106 may be a low compression foam, for example, 10-15% compression. The foam supports 106 may be formed of, for example, Accusorb™.

The upper housing 101 of the PAP device 100 is curved. To prevent the curvature of the upper housing 101 from causing the foam supports 106 to be more compressed at the sides, the foam supports 106 may include straight sides 119, as shown in FIGS. 5-8 and 5-9. The upper foam support 106 may also be shaped to have a corresponding curvature corresponding to the curvature of the upper housing 101 of the PAP device 100.

The chimney 109 encourages more laminar flow into the blower 105. The chimney 109 has a height of, for example, about 4 mm due to the limited space in the PAP device 100, although a taller chimney may improve acoustic performance. The diameter of the chimney is structured to match the inlet hole, for example, the diameter may be about 15 mm, about 16 mm, or about 17 mm but larger diameters may be used depending on the size of the blower and the inlet hole, for example, in a range of from 10-30 mm, 10-25 mm, or 10-20 mm.

Referring to FIG. 5-3, the blower includes a blower cover 111 having a blower inlet 127. An impeller 112 is provided for radially accelerating the air flow. The impeller 112 may be as shown and described in, for example, U.S. Patent Application Publication 2008/0304986 A1, the entire contents of which are incorporated herein by reference.

The blower 105 also includes a bottom cover 118 which supports an electromagnetic shield 108, see FIG. 5-2, adapted to protect the patient from electromagnetic fields emitted from the motor as described in more detail below. In the assembled motor, the motor magnet 117 and bearings 116 are inserted into the circular space within the stator 114 seen in FIG. 5-3. The bearings 116 surround the motor shaft, and the motor shaft extends through the central opening to allow attachment of the impeller 112. The magnet may be as shown and described in, for example, WO 2007/048205 A1 and WO 2007/048206 A1, the entire contents of each being incorporated herein by reference. The bearings 116 may be as shown and described in, for example, U.S. Patent Application Publication 2008/0304986 A1.

The blower 105 further comprises a printed circuit board (PCB) 115 that includes circuitry configured to control the operation of the blower 105. A stator 114 is coupled to the PCB 115. The stator 114 may be as shown and described in, for example, WO 2007/048205 A1 and WO 2007/048206 A1. An overmould 113 is provided between the stator 114 and the impeller 112. Referring to FIG. 5-2, the electromagnetic shield 108 may be attached to the bottom cover 118 to assist with dampening vibration. The electromagnetic force (EMF) shield 108 may have a circular flat shape with a diameter of, for example, 55 mm, and a thickness of, for example, 0.6 mm. The EMF shield 108 may be made from magnetically conducted material, for example, stainless steel 430. The EMF shield 108 may be adhered to the bottom cover 118 of the blower 105 by adhesive, for example, double sided pressure sensitive adhesive.

Referring to FIGS. 5-1, 5-2 and 5-12, the PAP system may include a PCB 163 in place of, or in addition to, the PCB 115. The PCB 163 may be provided in the housing 101, 102 and be separated from the blower 105 by a wall 164, that may be part of the upper housing 101, the lower housing 102, or a combination of the upper and lower housings 101, 102. The wall 164 may be flexible to increase the muffling of the housing 101, 102 and reduce the noise of the PAP system 100. The PCB may be connected to a wire, for example for providing power to the blower 105, by a grommet 165 that is attached to the housing 101, 102. The rigidity of the housing 101 and/or 102 may be increased in the grommet exit area and additional sealing may be provided between the housings 101, 102 at the grommet exit area. The grommet 165 may be integrated into the housing 101, 102 to improve the aesthetics and ergonomics of the PAP system 100.

In an alternative example, the PCB 163 may be removed from the housing 101, 102 and the power may be provided via the cable from a control, and the additional space in the housing 101, 102 may be used as an additional muffler.

Figures 5, 6:
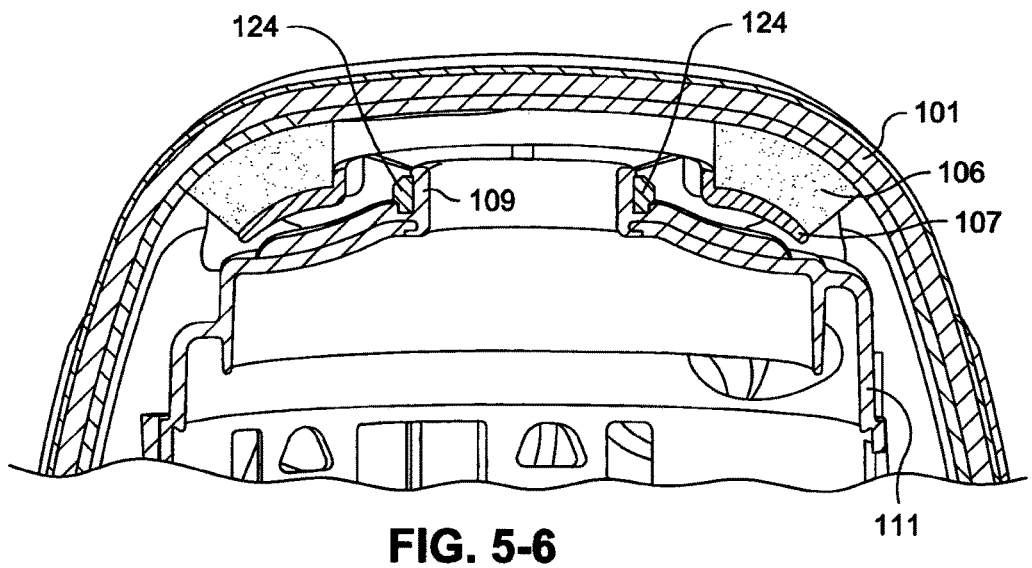
Figures 5, 6, 7:
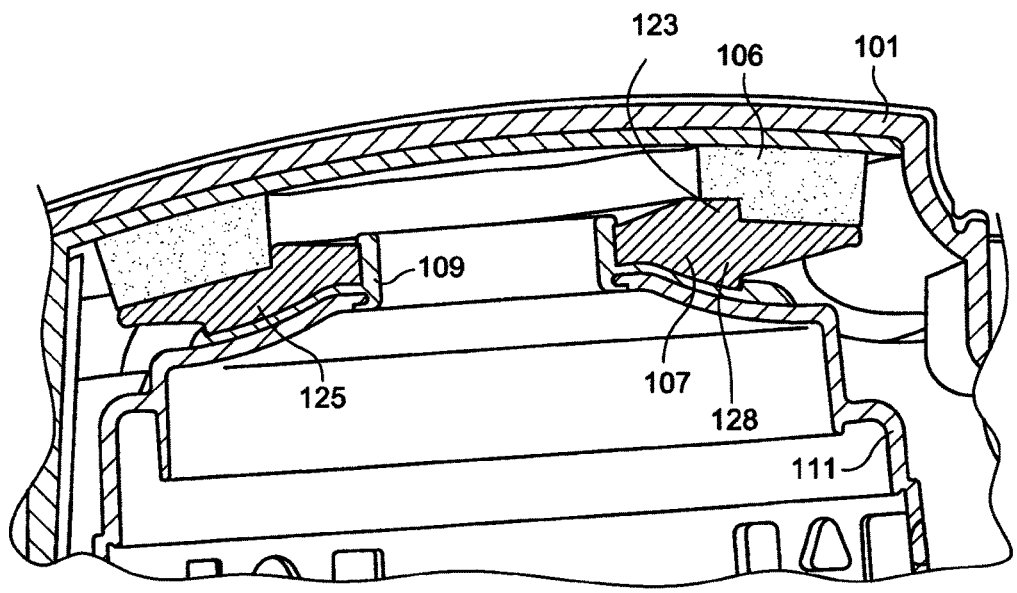

As shown in FIGS. 5-6, 5-8 and 5-9, the inlet cage 107 may include a ring 124 that is configured to be inserted around the chimney 109. The inlet cage 107 may also include ribs 125 that are configured to be received in recesses 126 (FIG. 5-5) in the chimney 109 to align the inlet cage 107 to support the upper foam support 106 in a fixed position above the blower 105 and establish the fixed inlet path to the chimney 109. However, other means of retaining the inlet cage in position in relation to the chimney 109 may be utilized, such as ribs on the chimney 109 and slots or grooves on the inlet cage 107, an interference fit or snap fit between the ring 124 and the chimney 109, clips, fasteners, etc. Furthermore, it should be appreciated that the inlet cage 107 may be made in other forms or shapes and still provide a fixed inlet to the blower inlet via the chimney 109 and/or support the foam supports 106. The inlet cage 107 comprises a foam locator 123 on an upper surface that engages the foam support 106 as shown in FIG. 5-7 to correctly position the foam on the inlet cage 107. A shorter rib 128 on the lower surface of the inlet cage 107 is provided at a position corresponding to the position of the foam locator 123 to correctly position the inlet cage 107 on the chimney 109.

False Chamber Example

Referring to FIGS. 6-1 and 6-2, the PAP device 100 may include a false chamber 110 added to the bottom of the lower housing 102. The false chamber 110 acts as a Helmholtz resonator and may have a volume of, for example, 40 ml. The ratio between the volume of the false chamber 110 and the volume of the housing 101, 102 of the PAP device 100 allows tuning of the noise generated by the PAP device 100. In an example, the ratio of the volume of the false chamber to the volume of the housing may be in the range of about 10% to 50%, preferably 20% to 40%, such as 25% to 30%. It should be appreciated that one of ordinary skill in the art that chambers having different volumes may be used. In addition, the false chamber 110 has a dampening effect on the vibration by acting as a spring.

PAP Device Example

Referring to FIGS. 7-1 to 7-12, a PAP device 100 according to certain examples is illustrated. As shown in FIGS. 7-1 and 7-2, the PAP device 100 comprises an upper housing 101 and a lower housing 102. A filter cover 103 is connectable to and disconnectable from the upper housing 101 to cover a filter described in more detail below. To reduce the perceived height of the PAP device 100, the filter cover 103 may include a scalloped detail or portion 138 in a region where the filter cover 103 connects to the upper housing 101 when in the connected position. The housing 101, 102 of the PAP device 100 may also have a curvature 137 at the rear to concentrate a portion of the volume of the housing 101, 102 at the rear of the PAP device 100 to reduce the overall volume and size of the housing 101, 102. The housing 101, 102 may also have raised base sides 139, as shown for example in FIGS. 7-1 to 7-3, to reduce the perceived size of the PAP device 100.

Referring to FIGS. 7-3 to 7-5, the PAP device 100 includes a blower, or flow generator, 105 provided within the housing 101, 102. The blower 105 may be similar to the blower discussed above with respect to certain examples disclosed in FIGS. 5-1 to 5-13. The upper housing 101 includes a filter inlet 131 having a retention feature, or rib, 132 for retaining a filter 140 that is provided over the filter inlet 131. The filter 140 may have a filter overmold 149 that retains the filter 140 along with the rib 132 in the filter inlet 131, as shown in FIG. 7-11. The upper housing 101 may also include air inlet clearances 152 through which air may be drawn into the filter inlet 131 by the blower 105.

An outlet connector 153 is attached to the housing 101, 102. The outlet connector 153 may be connected to, for example, the short outlet tube 9100 described above. As shown in FIGS. 7-4 and 7-5, the outlet connector 153 may comprise tabs 150 that are received in recesses 135 in the upper housing 101 and recesses 136 in the lower housing 102. The outlet connector 153 slides into the upper housing 101 vertically, and then is retained by connection of the lower housing 102 to the upper housing 101.

Figures 5, 6, 7, 8:
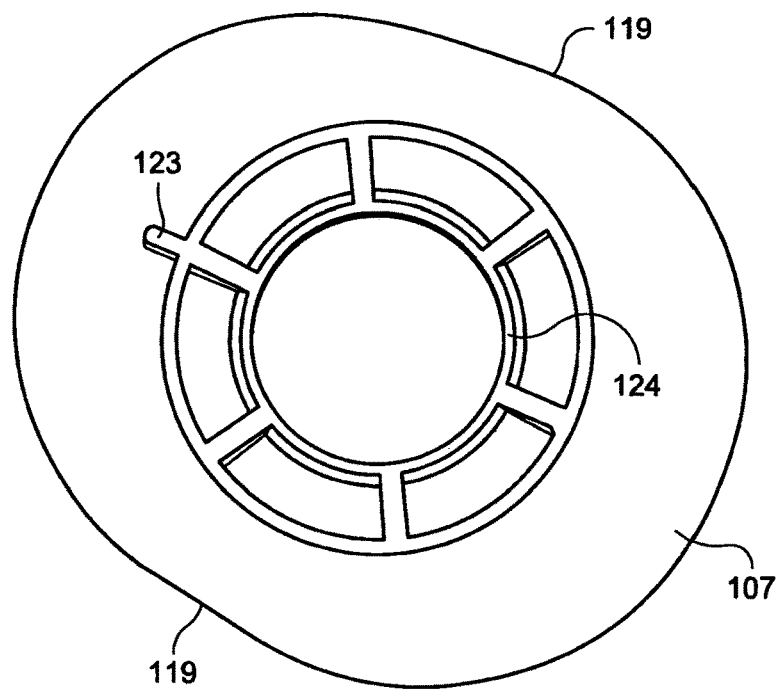
Figures 5, 6, 7, 8, 9:
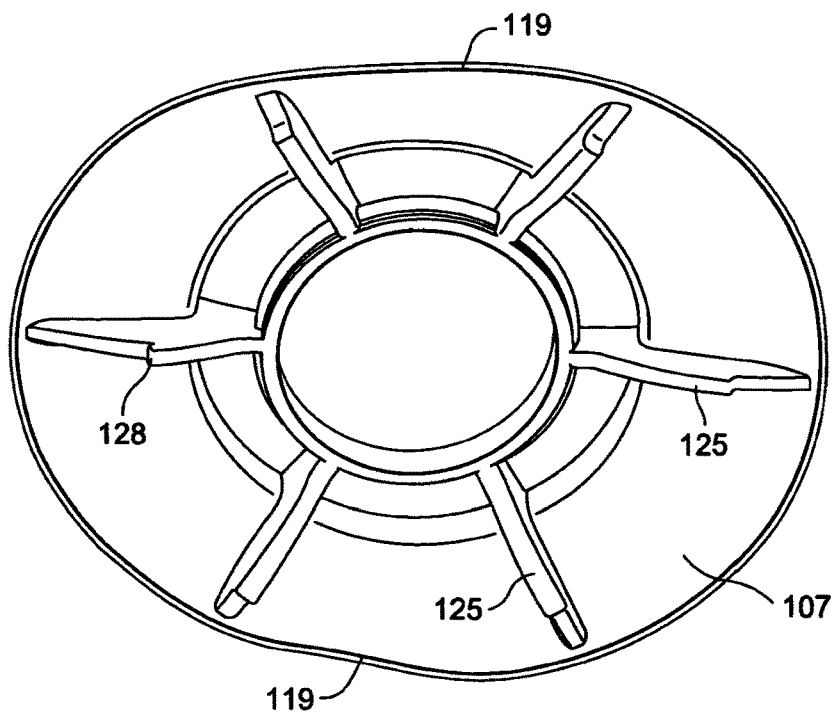
Figures 5, 6, 7, 8, 9, 10:
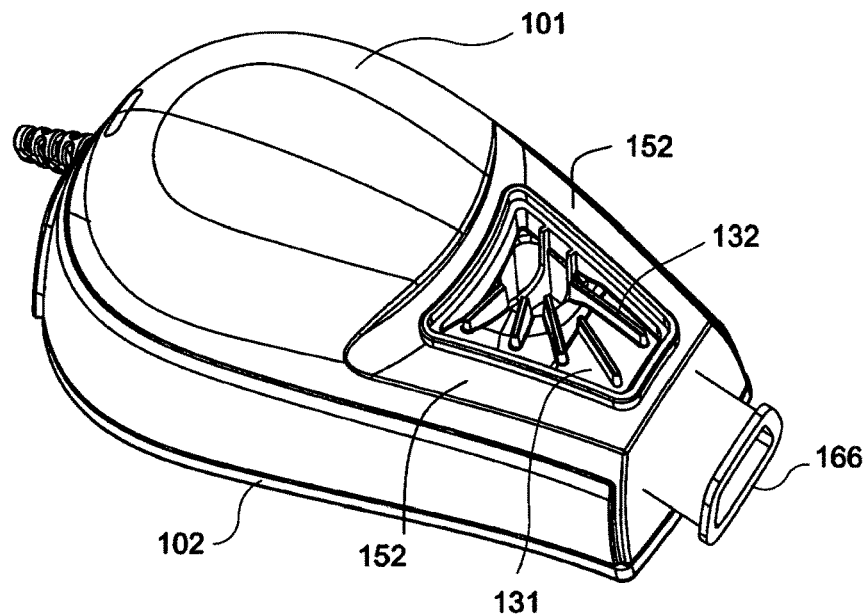

Referring again to FIG. 7-3 and FIGS. 7-6 to 7-9, the PAP device 100 includes an inlet elbow 142 that receives the flow of air from the filter inlet 131, as shown in FIGS. 7-10. A flow of air is drawn into the housing 101, 102 through the air inlet clearances 152 and into the filter inlet 131 and down through the inlet elbow 142, in a manner similar to the inlet tube 129 discussed above with respect to FIGS. 5-10 to 5-13. The lower end of the inlet elbow 142 terminates above the lower housing 102 with a gap as shown in FIG. 7-9. Once the airflow exits the lower end of the inlet elbow 142 it is dispersed in all directions, or 360°, into the internal area of the housing 101, 102 and travels up to the chimney 109 of the blower 105 and into the blower inlet 127. As shown in FIG. 7-7, the inlet elbow 142 may have a curved shape that may reflect back sound wavelengths to further reduce the noise generated by the blower 105. The inlet elbow 142 is preferably formed of a flexible or elastomeric material, for example silicone, to allow the expansion as the air flows therethrough to further assist with reducing noise output.

As shown in FIG. 7-3, the PAP device 100 includes an outlet muffler 143 that is connected to the blower outlet 151. The outlet muffler 143 includes an outlet muffler inlet 144 that is connected to the blower outlet 151. The outlet muffler 143 further comprises an outlet muffler chamber 146 having an extended portion 147 that extends around the inlet elbow 142 on a side opposite the outlet muffler inlet 144, as shown in FIGS. 7-6 and 7-10. The outlet muffler 143 is preferably formed of a flexible or elastomeric material, for example silicone, to allow the expansion as the air flows therethrough to further assist with reducing noise output. The outlet muffler 143 also includes an outlet muffler outlet 145 that is in sealing relationship with the outlet connector 153, as shown in FIGS. 7-5 and 7-9. As shown in FIG. 7-9, the inlet elbow 142 and the outlet muffler chamber 146 are in a nested relationship which allows the size of the outlet muffler chamber 146 to be increased, for example, in comparison to the muffler chamber 104 of the examples shown in FIGS. 5-1 to 5-13.

The housing 101, 102 of the examples shown in FIGS. 7-1 to 7-12 may have a larger volume than the housing 101, 102 described in the examples shown in FIGS. 5-1 to 5-13. The larger volume of the housing reduces the pressure drop of the blower 105 without affecting the acoustic performance of the PAP device 100. The perception of increased size due to the larger volume of the housing 101, 102 of the examples shown in FIGS. 7-1 to 7-12 may be mitigated by, for example, the scalloped portion 138 (FIG. 7-1) of the filter cover 103, the redistribution of the increased volume into the lower visibility regions of the PAP device 100, for example, the curvature 137 (FIG. 7-2) of the rear of the housing 101, 102, and the raised base sides 139 provided to the housing 101, 102.

The filter inlet 131 of the examples shown in FIGS. 7-1 to 7-12 may also have a larger area than a filter inlet 131 of the examples shown in FIGS. 5-1 to 5-13. This allows an increase in the filter area, which improves the pressure drop/swings performance of the blower 105. The air inlet clearances 152 of the examples shown in FIGS. 7-1 to 7-12 also provide improved pressure drop/swings performance compared to the air inlet clearances of the examples shown in FIGS. 5-1 to 5-13.

Deflecting Structure Example

Referring to FIGS. 8 and 9, the PAP device 100 may include a deflecting structure 148 to point the air inlet clearances 152 away from the user's ears to reduce the sound of the PAP device 100 heard by the user.

Transient Suspension Example

Referring to FIG. 10, a transient suspension system 160 for the blower 105 may be provided to prevent transmission of the vibration of the blower to the walls of the upper housing 101. The transient support system 160 may include a support for the blower 105 attached to bottom housing 102 that allows movement from side to side for the blower 105, but does not touch the sides of the upper housing 101. The transient support system 160 is adjacent to at least one side of the blower 105. The side to side movement will have little transmission in a downwards direction.

Figures 5, 6, 7, 8, 9, 10, 11:
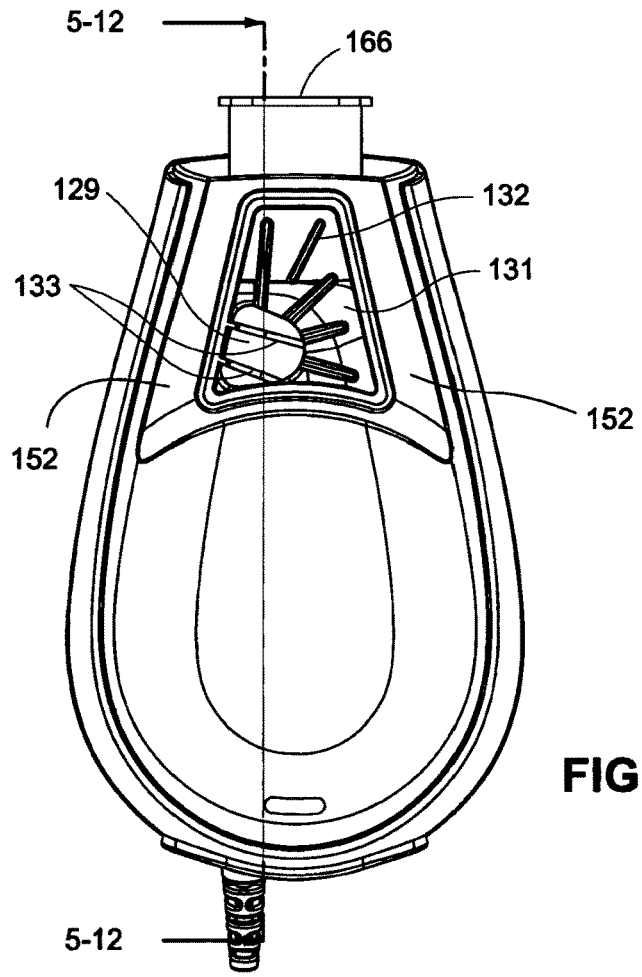

According to another example shown in FIG. 11, the transient suspension system may suspend the blower between a suspension band 161, for example a rubber band, so that bumps or feet 162 on the top and bottom of the blower 105 attach to the rubber band and each of the sidewalls of the upper housing 101. Vibration in the upwards and downwards direction is not transmitted in the side to side direction to the walls.

Blower Example

Figures 5, 6, 7, 8, 9, 10, 11, 12:
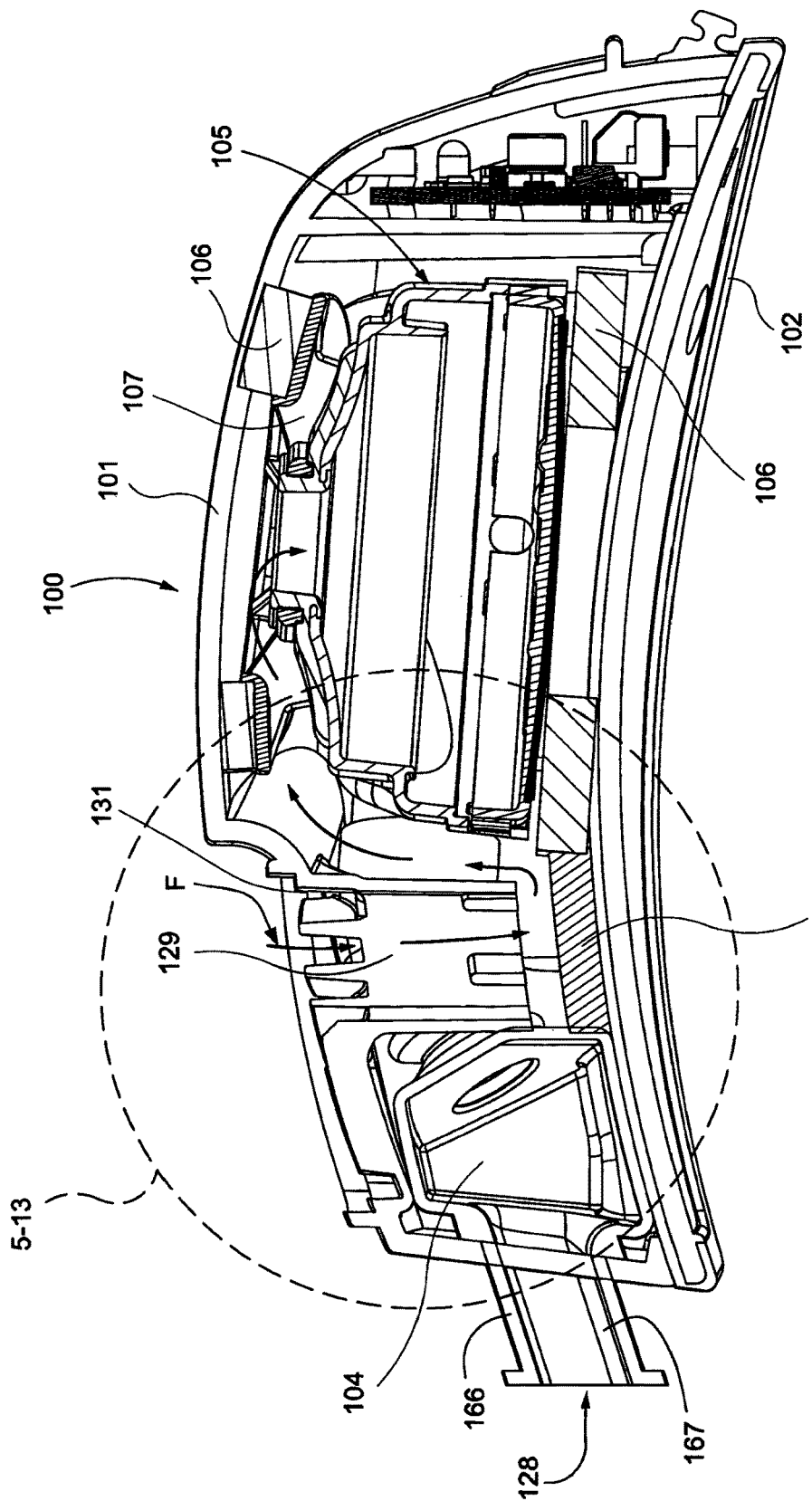
Figures 1, 6:
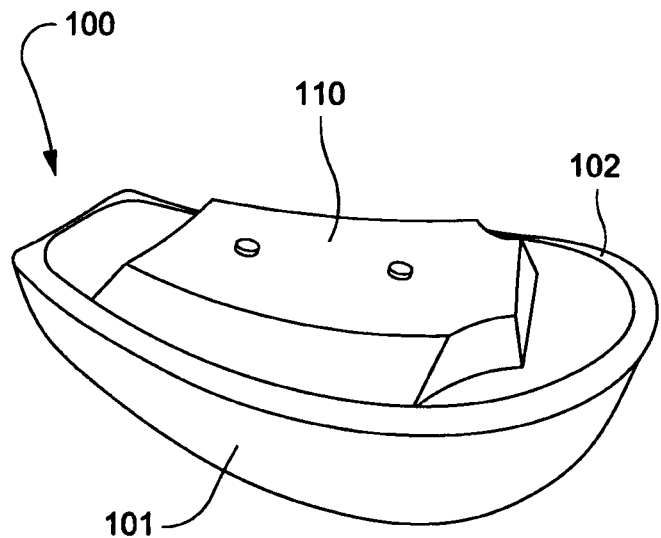
Figures 2, 6:
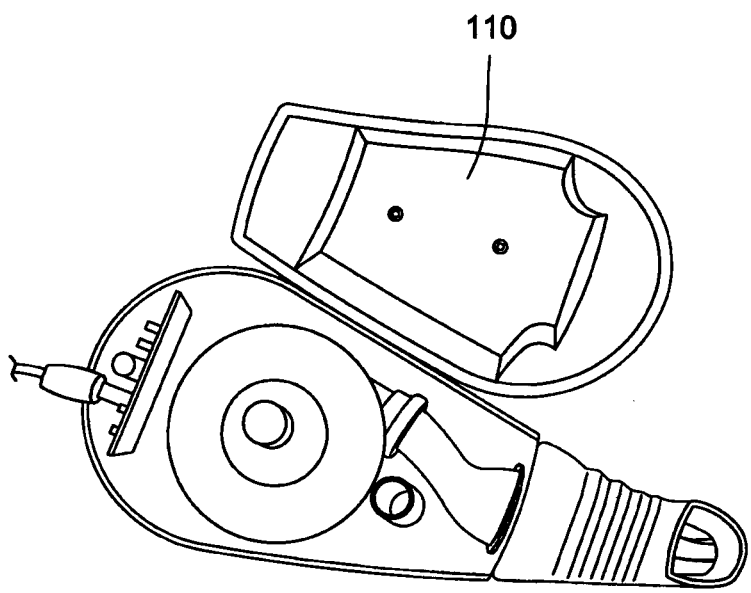
Figures 1, 7:
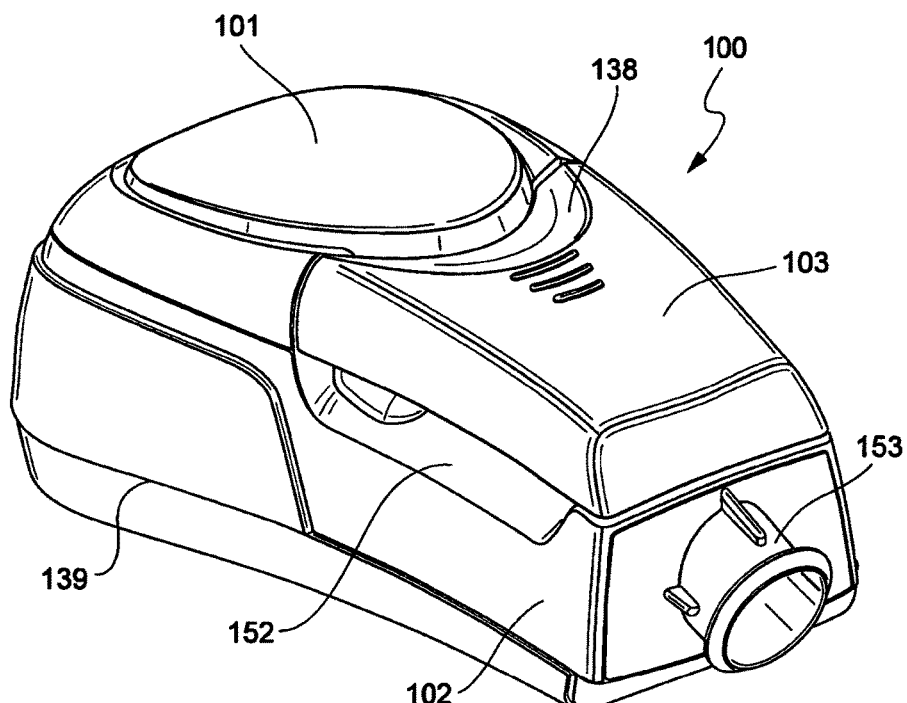
Figures 2, 7:
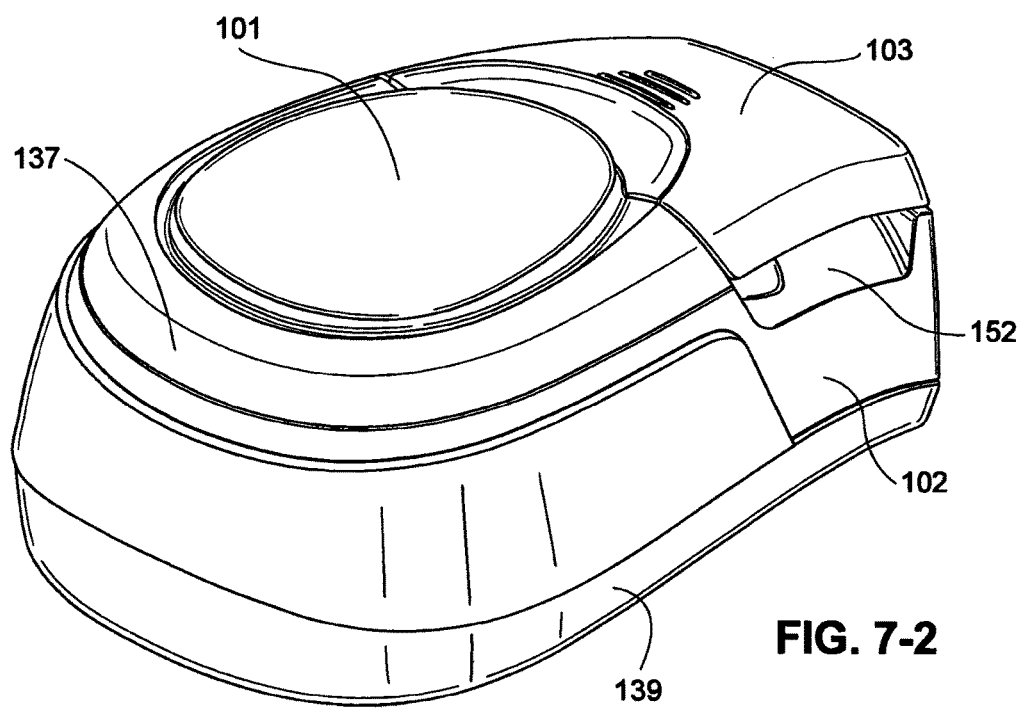
Figures 3, 7:
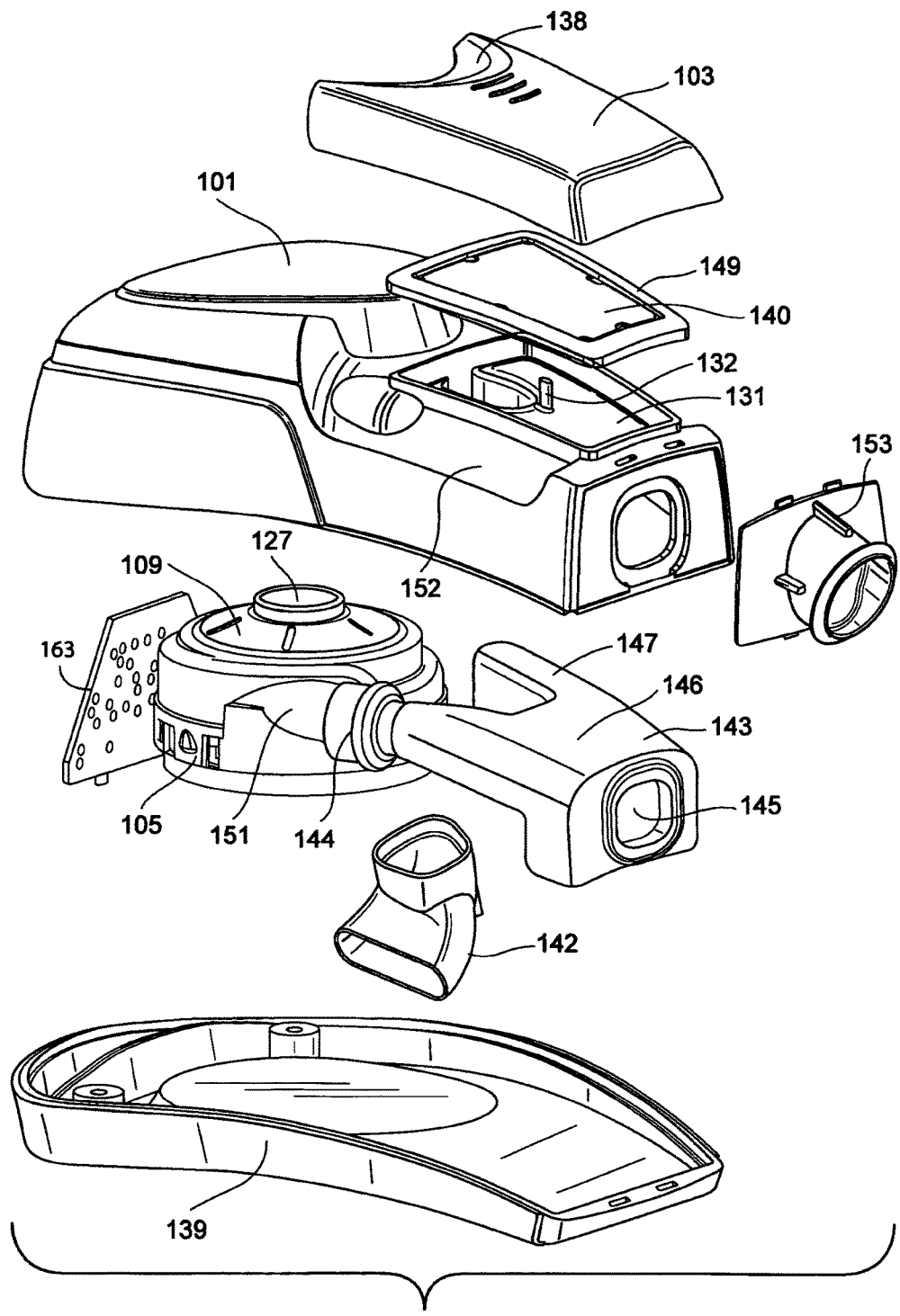
Figures 4, 7:
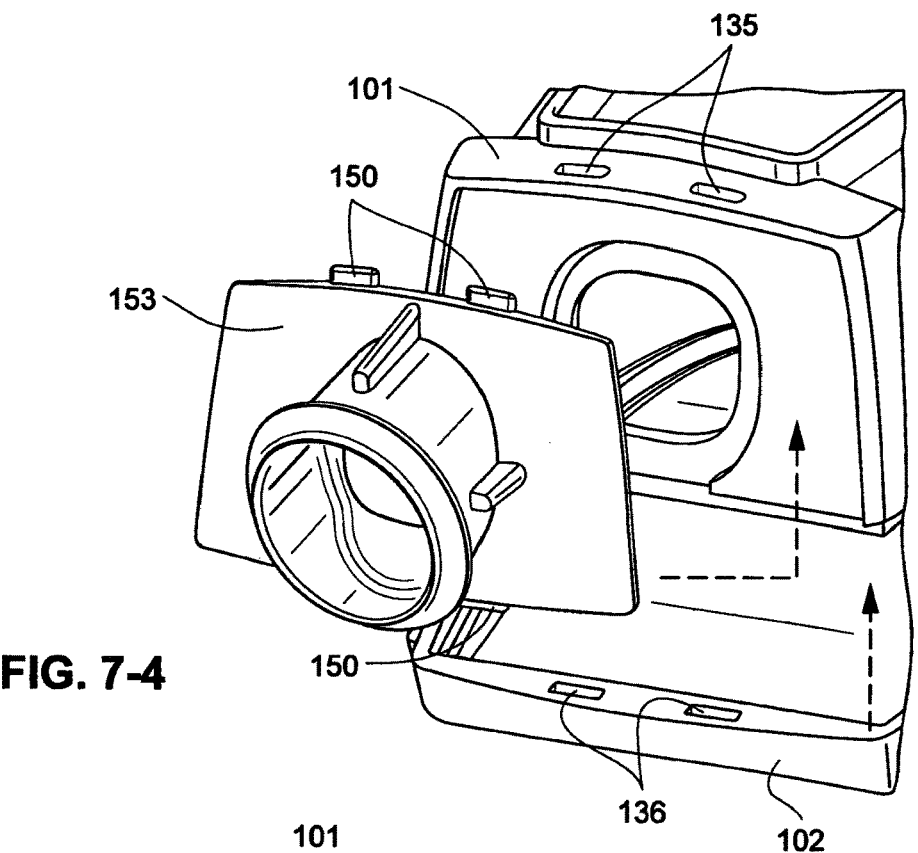
Figures 5, 7:
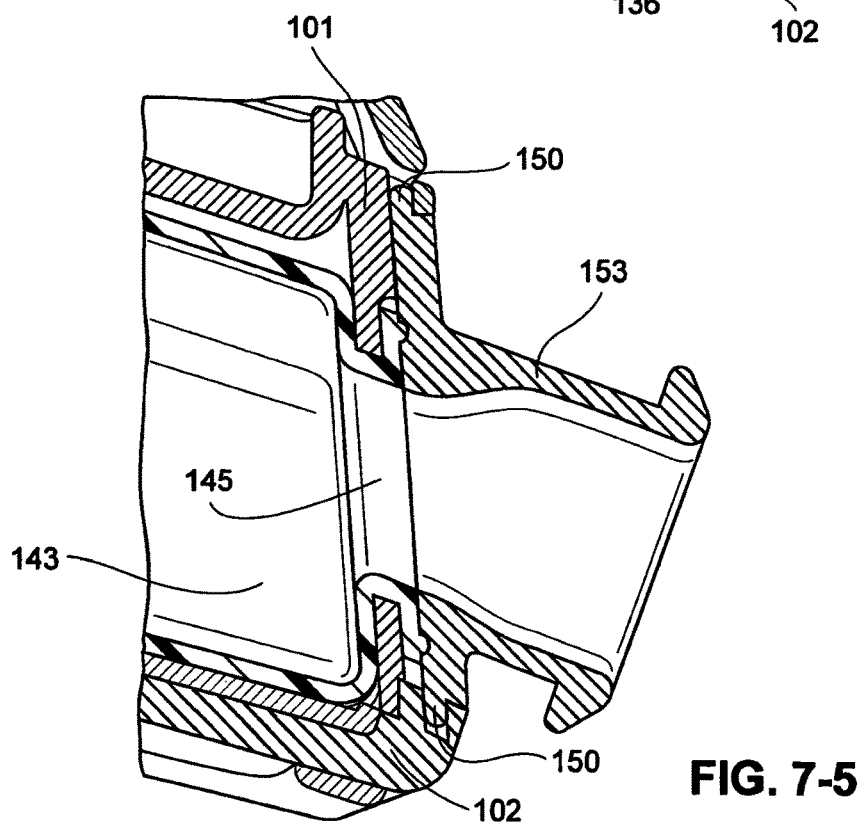
Figures 7, 8, 9, 10:
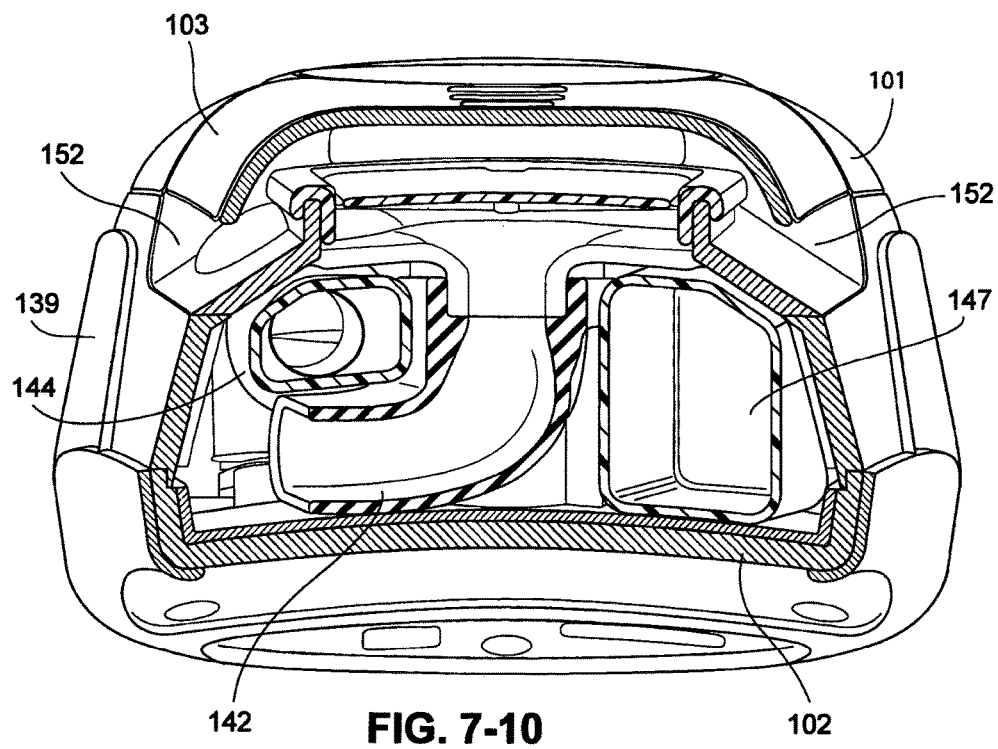
Figures 7, 8, 9, 10, 11:
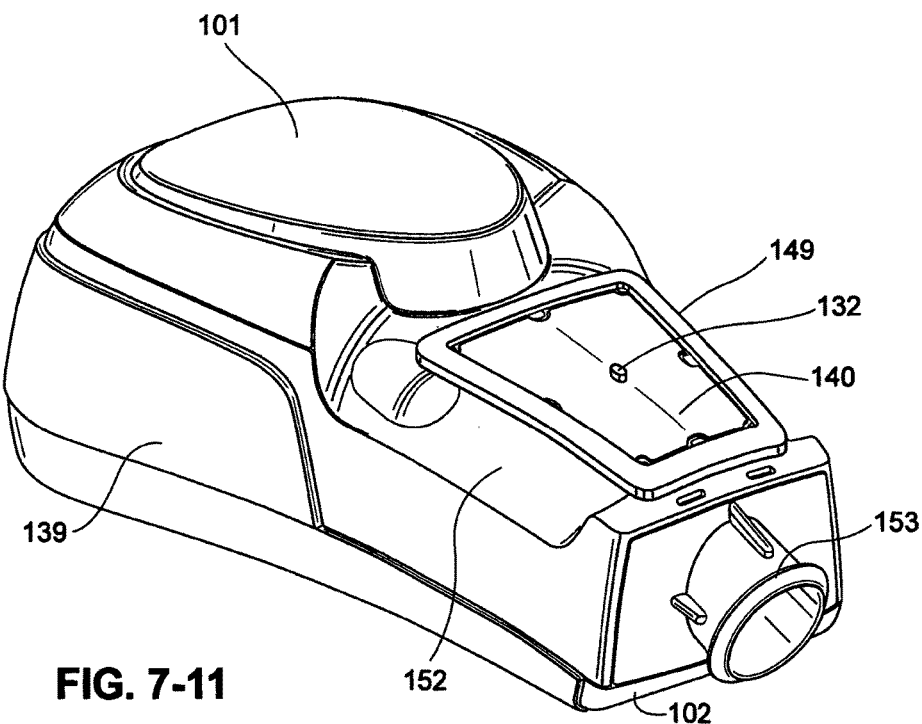
Figures 7, 8, 9, 10, 11, 12:
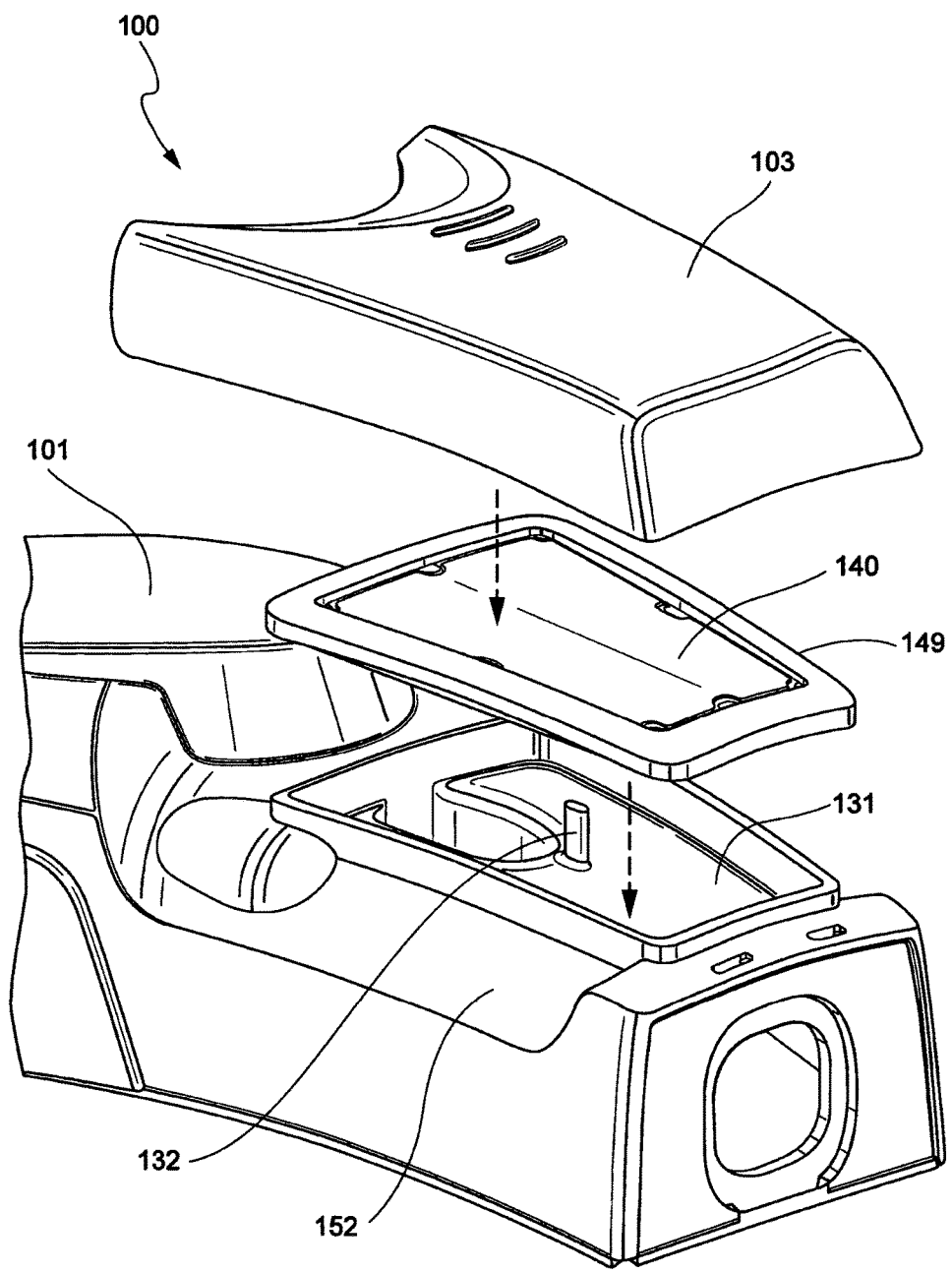
Figure 8:
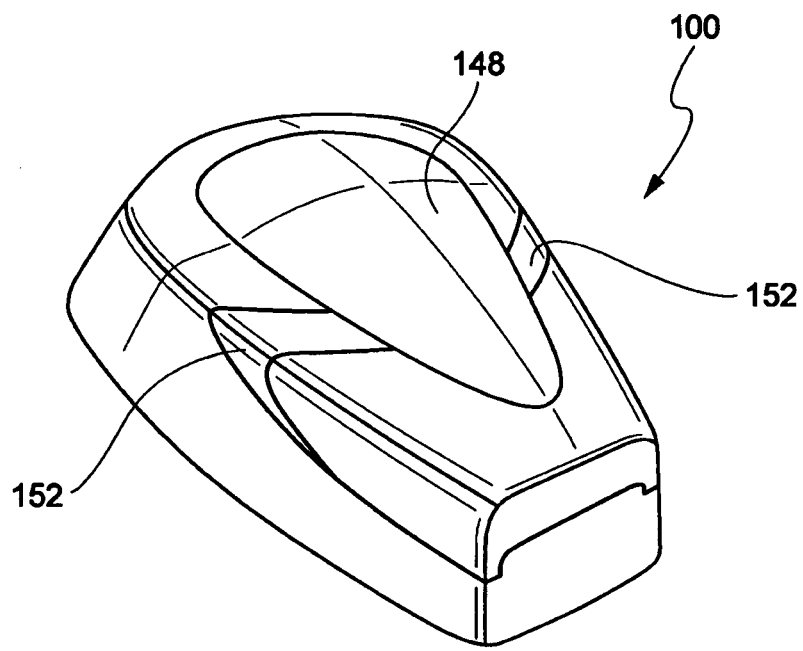
Figure 9:
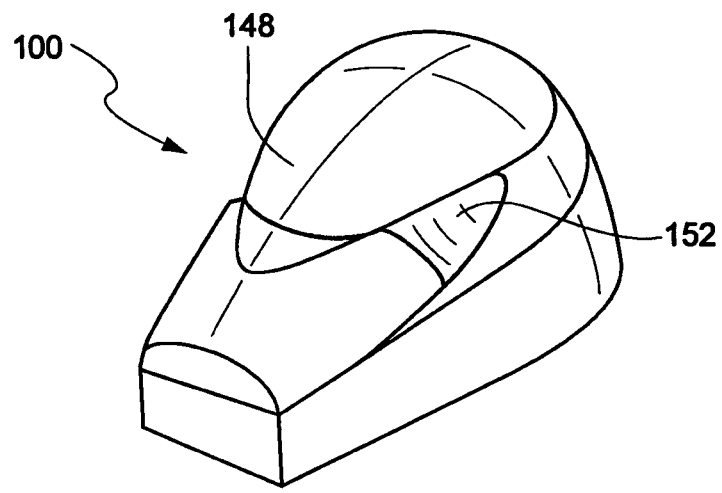
Figure 10:
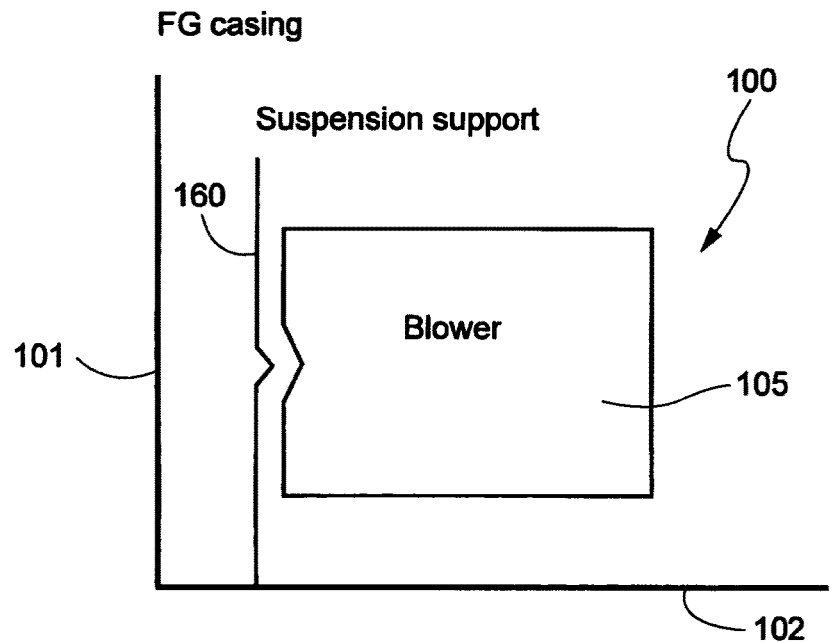
Figure 11:
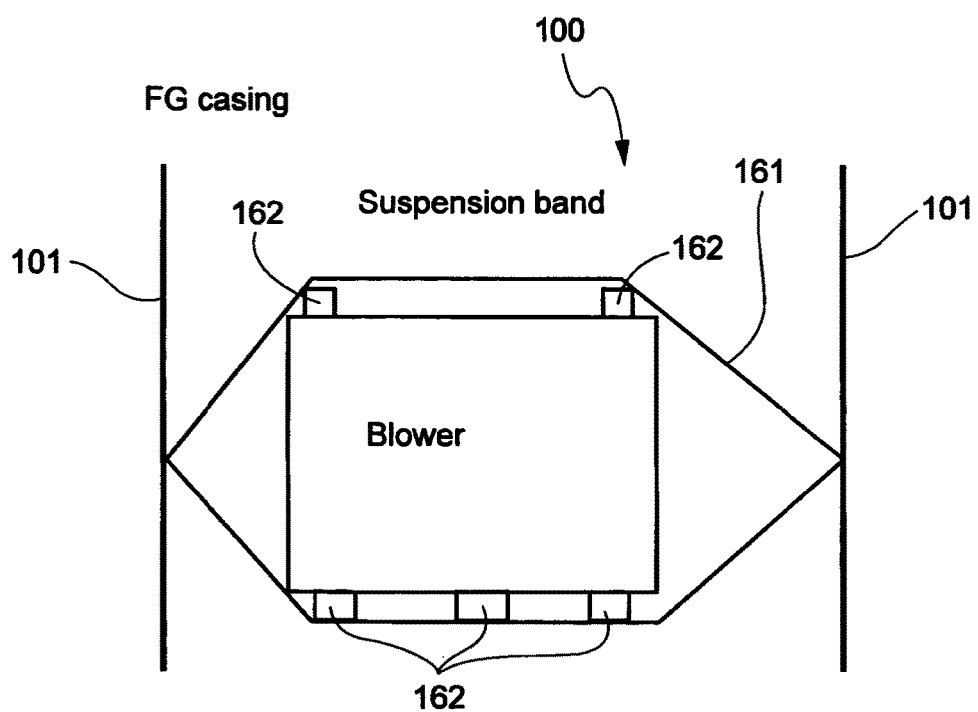
Figure 12:
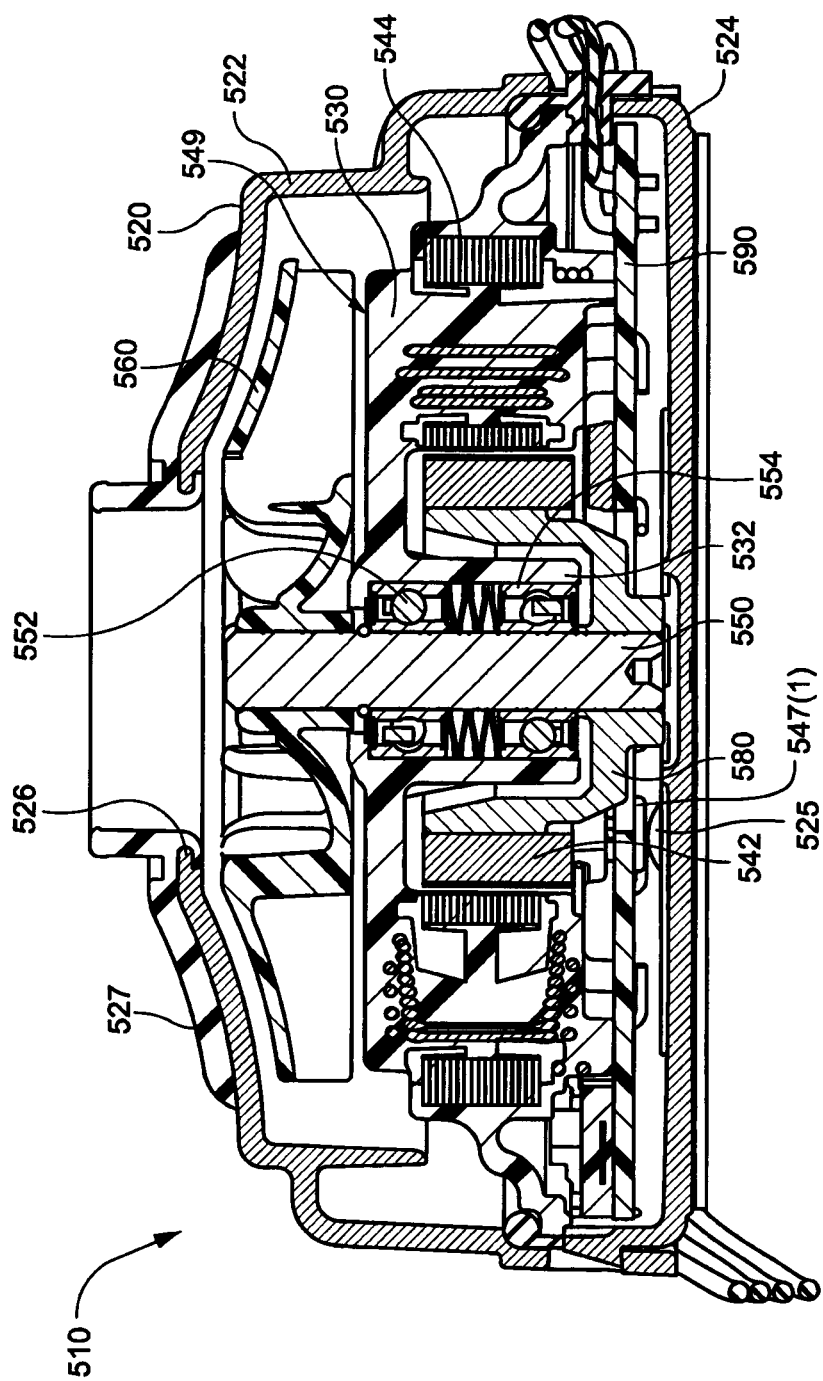

FIG. 12 illustrates a blower 510 as described in greater detail in PCT Application No. PCT/US2010/003010. As illustrated, the blower 510 includes a housing 520 with first and second housing parts 522, 524, a stationary component 530 (e.g., constructed of plastic such as LCP) including an overmold with a stator assembly 544 to form a one-piece overmolded stationary assembly 549, magnet 542 coupled to the rotor or shaft 550 by magnet support 580, impeller 560 coupled to an end portion of the shaft 550, and a printed circuit board assembly (PCBA) 590 for motor control. The shaft or rotor 550 is supported by bearings 552, 554 in a tube portion 532.

Increased Bearing Bore Size

As shown in FIG. 12 and further described in PCT Application No. PCT/US2010/003010, the interior surface of the tube portion 532 of the stationary component 530 is structured to retain and align bearings 552, 554 that rotatably support the shaft 550. The bearing 552 positioned closest to the impeller may be press-fit into the tube portion 532 (i.e., press-fit outer race of the bearing to the tube portion).

Figure 13:
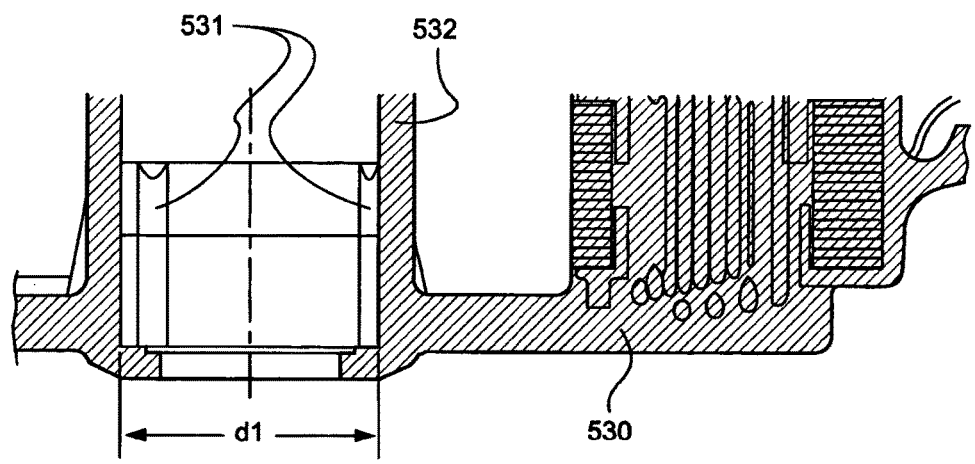

In an alternative example, as shown in FIG. 13, the bore size or diameter of the tube portion 532 can be modified, e.g., in the side closest to the impeller the bore can be increased (e.g., stepped or flared) to provide additional space to accept adhesive for retaining the bearing 552 closest to the impeller within the tube portion 532, i.e., in addition to or instead of press-fitting. That is, the diameter of the bore in the side closest to the impeller may be opened to an appropriate size to permit the use of adhesive for retention. For example, the diameter d1 in FIG. 13 may be increased by about 0.005 to 0.025 mm, e.g., 0.015 mm, to accept adhesive. Such increase may be a stepped increase with respect to the remaining tube portion, or may be a flared increase to the desired diameter. In an example, the diameter d1 may be about 9.005 to 9.025 mm, e.g., 9.015 mm. However, it should be appreciated that other suitable bore diameters are possible.

Also, the interior surface of the tube portion closest to the impeller may also include one or more elongated protrusions 531, e.g., three protrusions, to enhance retention. The protrusions protrude into the cavity of the tube portion creating an obstruction the outer race of the bearing will have to overcome in order to be able to move out of the tube portion or bearing bore once installed. That is, the protrusions effectively make the tube portion smaller than the outer race or outer diameter of the bearing.

Such retention features assisted in eliminating or reducing acoustic tonal peaks in use.

Bearing Cartridge

Figure 29:
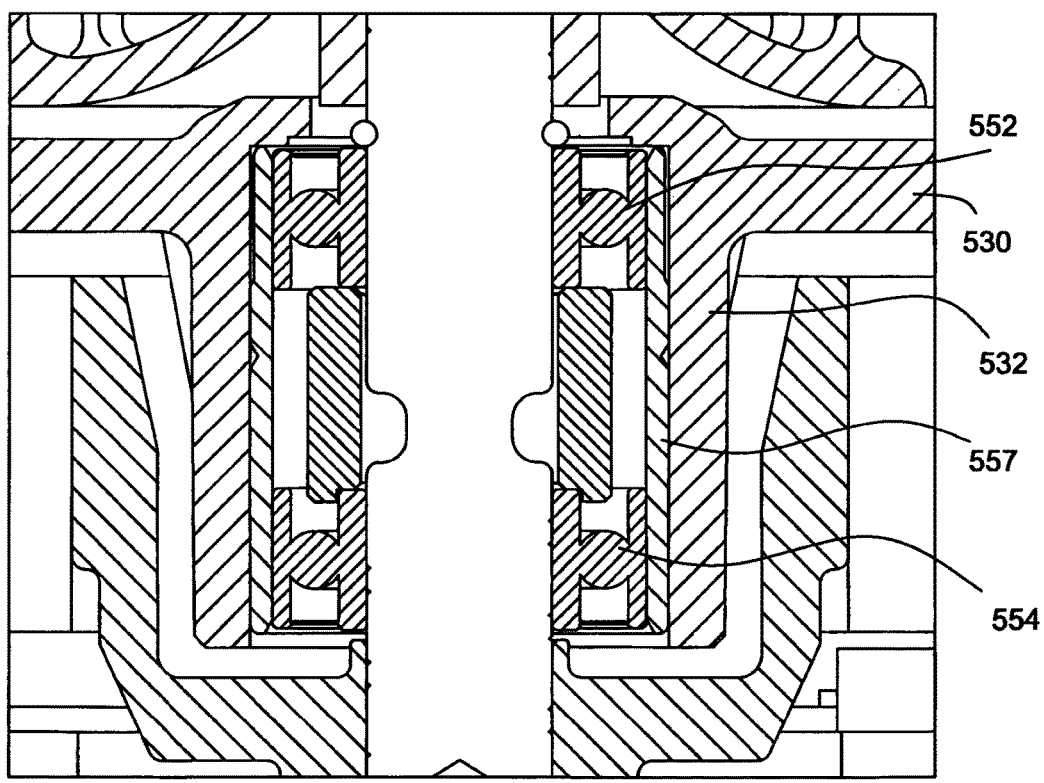
FIG. 29 is a cross-sectional view showing a bearing cartridge according to an example of the disclosed technology.

In an alternative example, as shown in FIG. 29, the bearing assembly of bearings 552, 554 may be provided within a cartridge 557 adapted to be inserted into the tube portion 532 of the stationary component 530. In contrast to individual bearings, the bearing cartridge reduces assembly steps on the blower assembly line and may eliminate a need for bonding.

Groove in Shaft

As noted above and further described in PCT Application No. PCT/US2010/003010, the shaft or rotor 550 is rotatably supported with the tube portion 532 by bearings 552, 554.

Figure 14A:
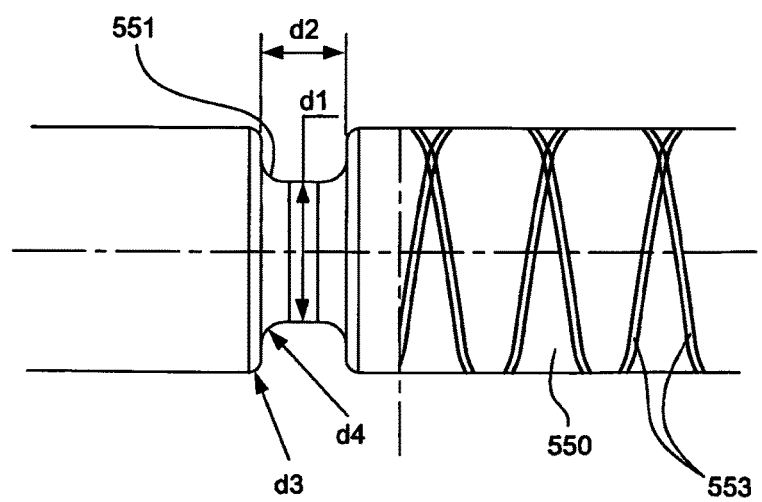
FIG. 14A is an enlarged plan view showing a shaft of a blower according to an example of the disclosed technology.
Figure 14B:
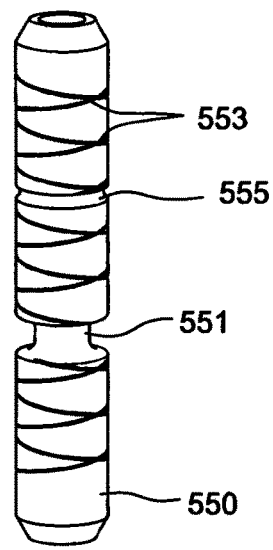
FIG. 14B is a perspective view of the shaft of FIG. 14A.
Figure 14C:
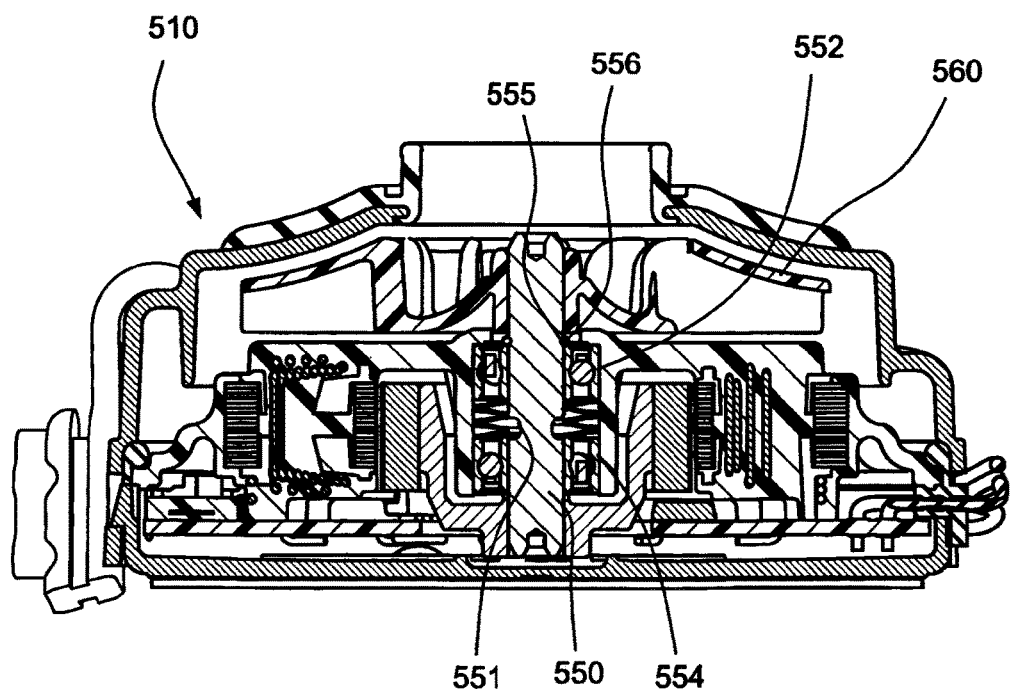
FIG. 14C is a cross-sectional view of a blower including the shaft of FIG. 14A according to an example of the disclosed technology.

In an alternative example, as shown in FIGS. 14A and 14B, at least one annular groove 551 may be provided to the shaft or rotor 550 and adapted to be positioned between the bearings 552, 554 or along a length of the shaft that is adjacent the bearings in use. FIG. 14C shows an example of such shaft within a blower 510. Such groove 551 is structured to reduce shaft stiffness and increase loss factor in order to attenuate the rotor mechanical resonances, lower the magnitude of the imbalance, and/or reduce bearing frequency peaks in the blower narrow band acoustics in use. In use, the grooved shaft provides loss of frequency and amplitude in the blower narrow band acoustics compared to a groove-less shaft.

In an example, as shown in FIG. 14A, d1, the diameter of the groove in the shaft or rotor, may be between about 50% and about 95%, between about 50% and about 75%, preferably between 60% and about 60% and about 70%, e.g., about 66%, of the shaft or rotor outer diameter and d2, the width of the groove, may be between about 20% and about 50%, preferably between about 30% and about 40%, e.g., about 33%, of the shaft or rotor outer diameter. For example, as shown in FIG. 14A, d1 may be between about 2 mm and 2.5 mm, e.g., about 2.3 mm, d2 may be between about 1 mm and about 2 mm, e.g., about 1.5 mm, the radius of curvature at d3 may be between about 0.1 mm and about 0.5 mm, e.g., about 0.2 mm, and the radius of curvature at d4 may be between about 0.25 mm and about 0.75 mm, e.g., about 0.5 mm. However, it should be appreciated that other suitable dimensions of the shaft or rotor are possible.

It should also be appreciated that the shaft may include one or more annular grooves along its length (e.g., 1, 2, 3, or more grooves), and such one or more annular grooves may include suitable dimensions to reduce shaft stiffness. Also, the size of the grooves (e.g., length and depth) may be varied with respect to one another to adjust shaft flexibility. The one or more grooves are adapted to be positioned between the bearings, and the positioning of such grooves along the shaft between the bearings may be adjusted.

In an example, dimensions of the groove (e.g., length, depth, radius) may be selected to enhance flexibility of the shaft while maintaining structural strength of the shaft or rotor, e.g., flexibility without breaking or deforming. In an example, the diameter of the groove may be about 50-95%, about 50-80%, about 50-60% of the diameter of the shaft or rotor. However, other suitable dimensions are possible (e.g., diameter of the groove may be greater than 90% of the diameter of the shaft or rotor), e.g., depending on the material of the shaft or rotor.

As shown in FIGS. 14A and 14B, smaller grooves 553 may be provided along the length of the shaft 550. In the illustrated example, the grooves 553 are arranged along the shaft in a double helix configuration. However, the grooves may be provided to the shaft in other suitable configurations. In an example, the grooves may be provided to enhance retention of the impeller 560, e.g., prevent thread off.

Also, as shown in FIGS. 14B and 14C, a smaller annular groove 555 may be provided receive a retaining ring 556 structured to maintain the shaft or rotor 550 within the tube portion.

Additional PCBA Retention Features

Figure 15:
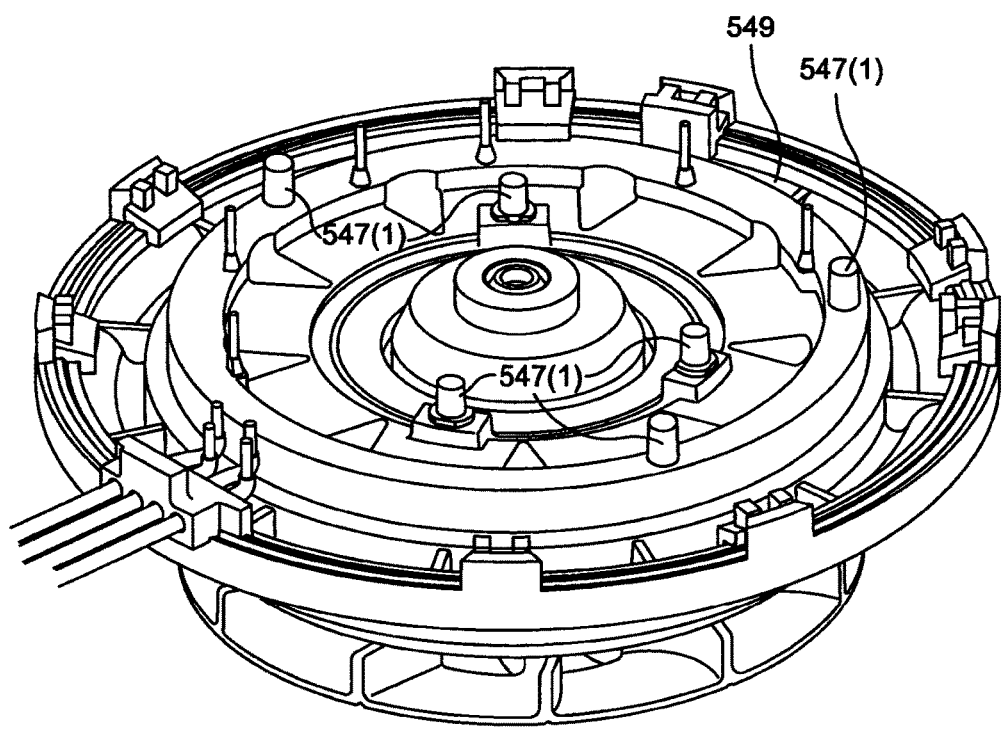
FIG. 15 is a perspective view of an overmolded stationary component and stator assembly according to an example of the disclosed technology.

As shown in FIG. 15 and further described in PCT Application No. PCT/US2010/003010, the overmolded stationary assembly 549 includes a plurality of pin-type mounting protrusions 547(1) that are adapted to engage within corresponding holes provided in the PCBA 590 to precisely position and align the PCBA 590 and its attendant components accurately with respect to the assembly 549 and its integrated stator assembly. The arrangement is processed to form heads on the tips of one or more of the protrusions 547(1), e.g., using heat staking, which forms the protrusions 547(1) into rivets to securely mount the PCBA 590 to the assembly 549.

In an example, the number of pin-type mounting protrusions 547(1) provided to the overmolded stationary assembly 549 and corresponding holes provided in the PCBA 590 (also referred to as heat stakable retention features) may be three or more, e.g., three mounting protrusions and corresponding holes provided along the inner diameter of the PCBA and three mounting protrusions and corresponding holes provided along the outer diameter of the PCBA. It should be appreciated that more than six protrusions or even one or two protrusions are possible. Such retention features may reduce frequency peaks in the blower narrow band acoustics.

Figure 16:
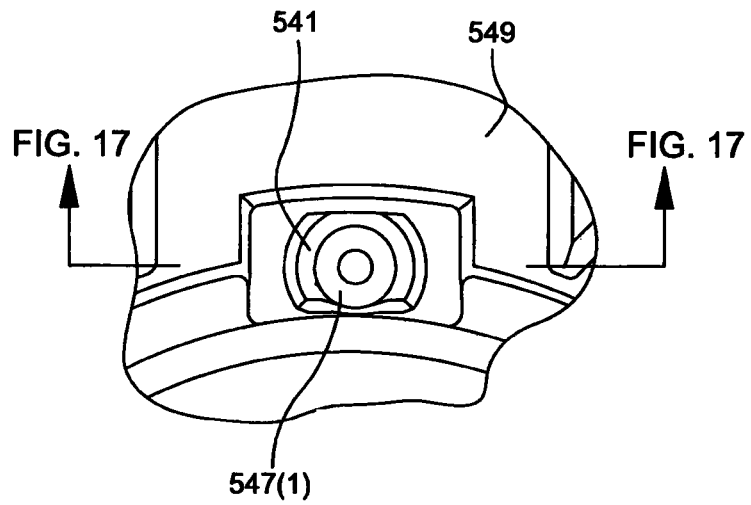
FIG. 16 is a top view of a PCBA mounting protrusion according to an example of the disclosed technology.
Figure 17:
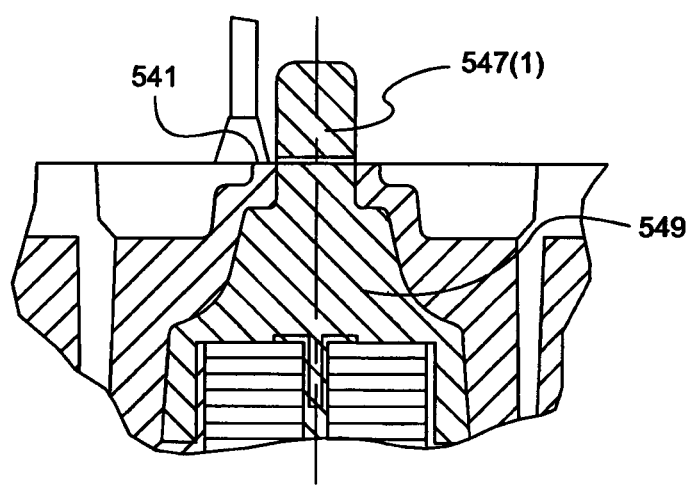
FIG. 17 is a cross-sectional view of the PCBA mounting protrusion shown in FIG. 16.
Figure 18A:
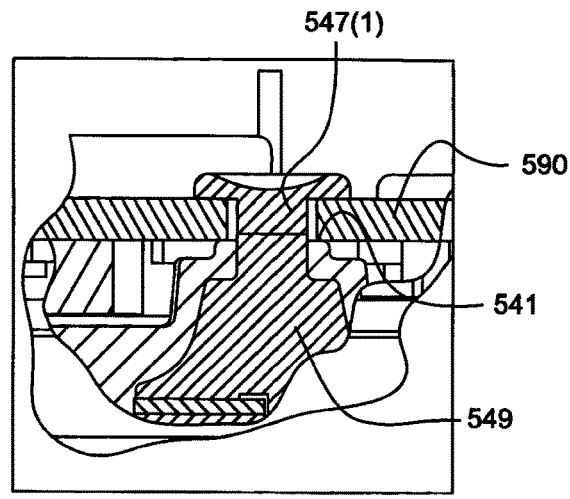
FIG. 18A is a cross-sectional view showing heat staking assembly of a PCBA to a stationary assembly according to an example of the disclosed technology.

FIGS. 16 and 17 show an example of a pin-type mounting protrusions 547(1) provided to the overmolded stationary assembly 549 and the raised surface 541 adjacent the protrusion adapted to the support the PCBA 590. FIG. 18A shows the protrusion 547(1) after it is processed, e.g., using heat staking, to form a head on the tip of the protrusion so as to securely mount the PCBA 590 to the assembly 549.

Figure 18B:
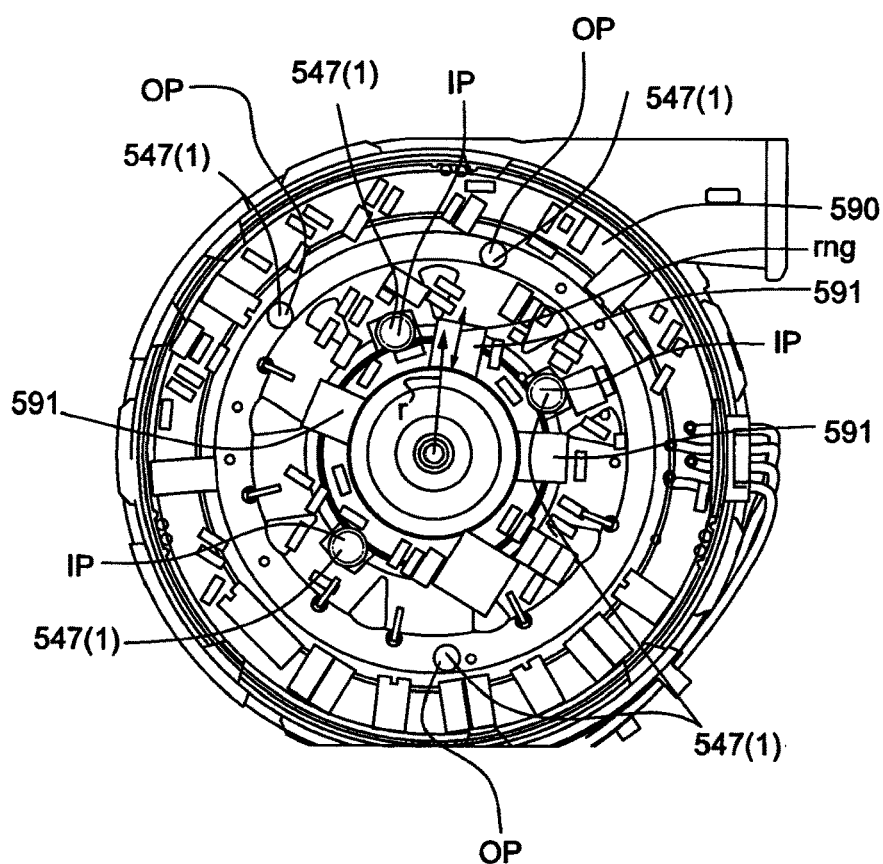
FIGS. 18B and 18C show Hall sensors of a PCBA in relation to PCBA mounting protrusions according to an example of the disclosed technology.
Figure 18C:
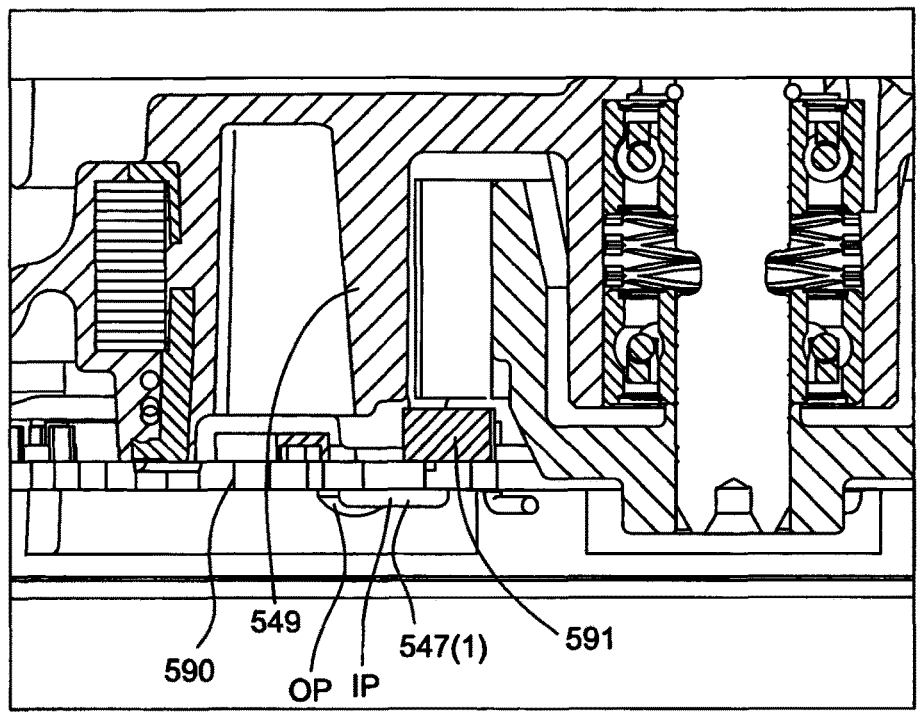

FIG. 18B shows an overmolded stationary assembly 549 including six pin-type mounting protrusions 547(1), i.e., three inner protrusions IP adapted to support an inner diameter of the PCBA 590 and three outer protrusions OP adapted to support an outer diameter of the PCBA 590. As shown in FIGS. 18B and 18C, the three inner protrusions IP are provided near Hall sensors 591 positioned along an inner diameter of the PCBA so as to enhance support of the inner diameter of the PCBA, i.e., Hall sensors relatively heavy and/or larger compared to most of the other components on the PCBA. As illustrated, inner protrusions IP are provided between adjacent Hall sensors 591, however other suitable arrangements are possible. The three inner protrusions IP reduce specific acoustic tones by damping the vibration of the inner portion of the PCBA.

In an example, as shown in FIG. 18B, both the inner protrusions IP and the Hall sensors 591 are located along a radius r within a predetermined range mg with respect to one another, e.g., rng about 5-30 mm, e.g., 5-10 mm. The inner protrusions IP and the Hall sensors 591 may be 10-50 mm from the center.

As shown in FIGS. 18B and 18C, the inner protrusions IP are staked to a lower height than the outer protrusions OP to provide clearance for bumps 525 on the inside of the second housing part or base cover 524 (e.g., see FIG. 12). The bumps 525 are structured to stop the cover 524 from deflecting into contact with the support or hub 580. The bumps 525 are not in contact with any other components during normal operation to reduce noise.

To accomplish the reduced staked height of the inner protrusions IP, the tops of the inner protrusions are concave to reduce the top center area of the protrusions while keeping a thicker material cross section in the location that is in shear stress at the PCBA hole inner diameter (e.g., see FIG. 18A). The outer diameter of the staked head of the protrusion is increased to provide an area for extra material to flow.

Chimney Provided to First Housing Part

Figure 19:
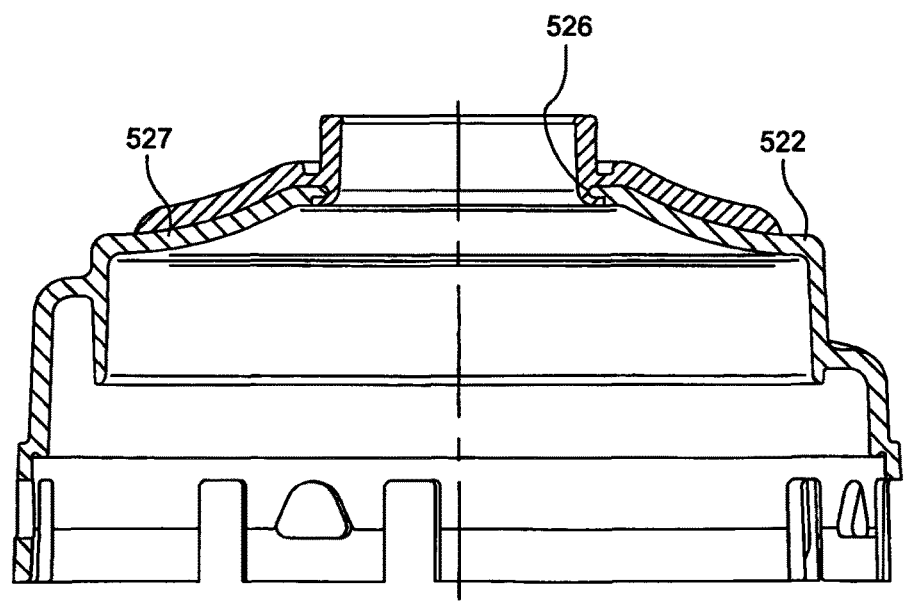
FIG. 19 is a cross-sectional view of a first housing part with overmolded chimney according to an example of the disclosed technology.

As shown in FIG. 12 and further described in PCT Application No. PCT/US2010/003010, a chimney or inlet tube portion 527 may be provided to the inlet 526 of the first housing part 522. The chimney is structured to reduce turbulent noise with no significant restriction to the air flow provided to the inlet. The chimney 527 (e.g., constructed of TPU alloy, e.g., TPE, or other suitable material) may be overmolded to the first housing part 522. FIG. 19 is an isolated view of the first housing part 522 with overmolded chimney 527.

Such chimney may help to improve acoustic damping of the first housing part and reduce acoustic sound power levels, e.g., reduce average $3^{rd}$ octave acoustic sound power levels, e.g., by 2 dBA.

Blower Bracket

Figure 20:
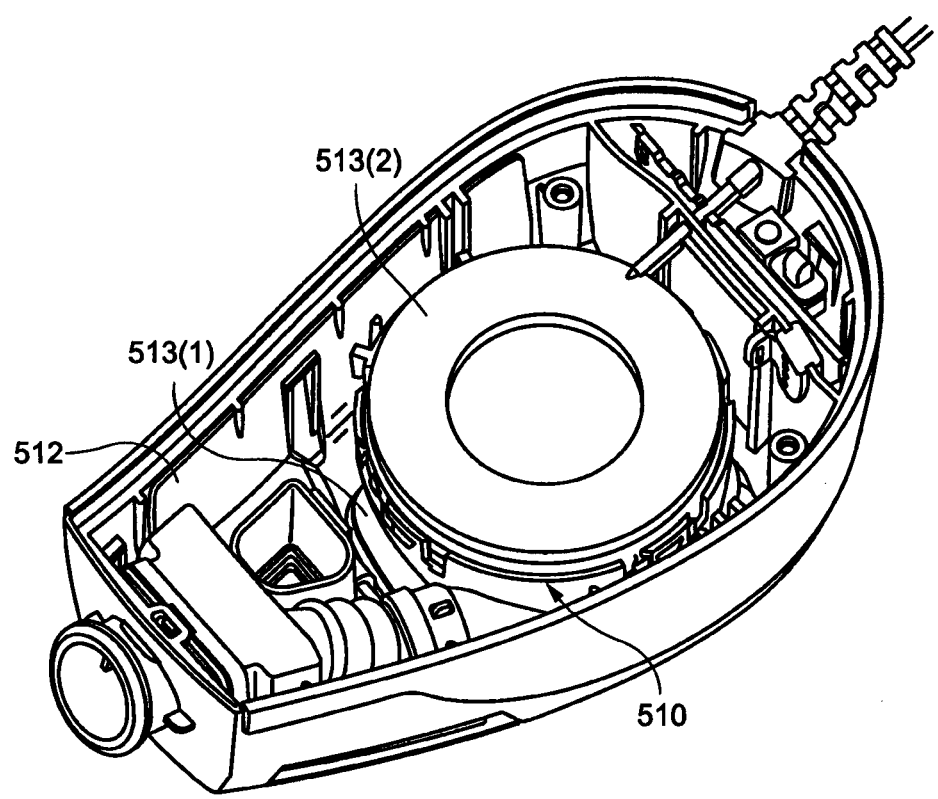
FIG. 20 is a perspective view showing a blower mounted within the casing of a PAP device according to an example of the disclosed technology, the casing shown with no cover.
Figure 21:
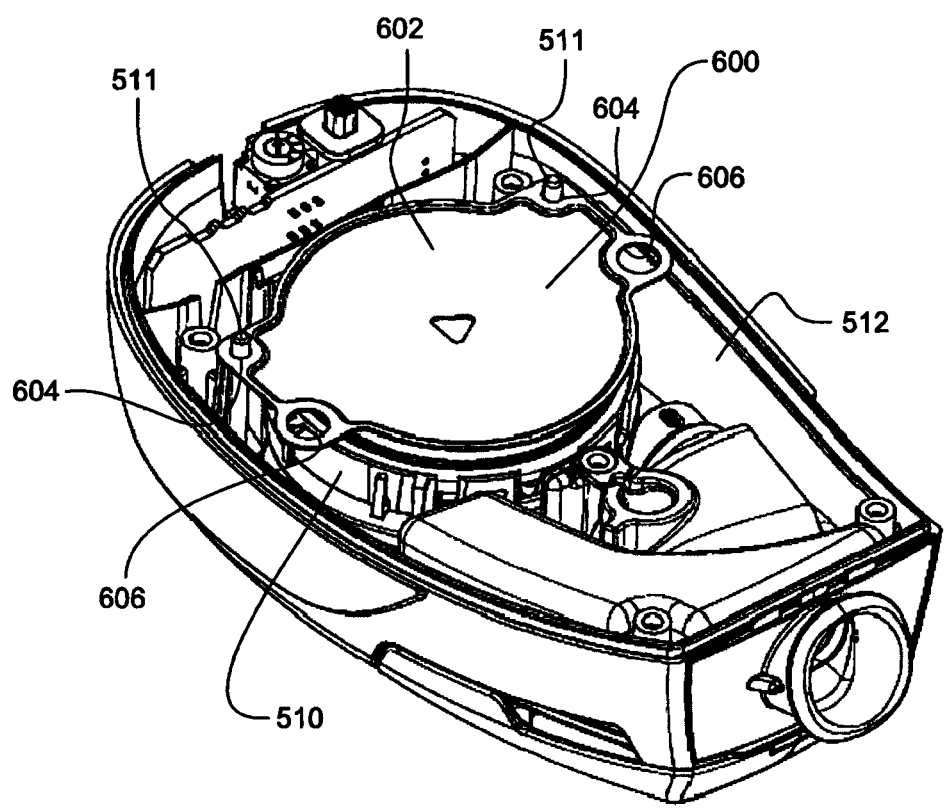
FIG. 21 is a perspective view showing a blower located and aligned within the casing of a PAP device by a blower bracket according to an example of the disclosed technology, the casing shown with no cover.
Figure 22:
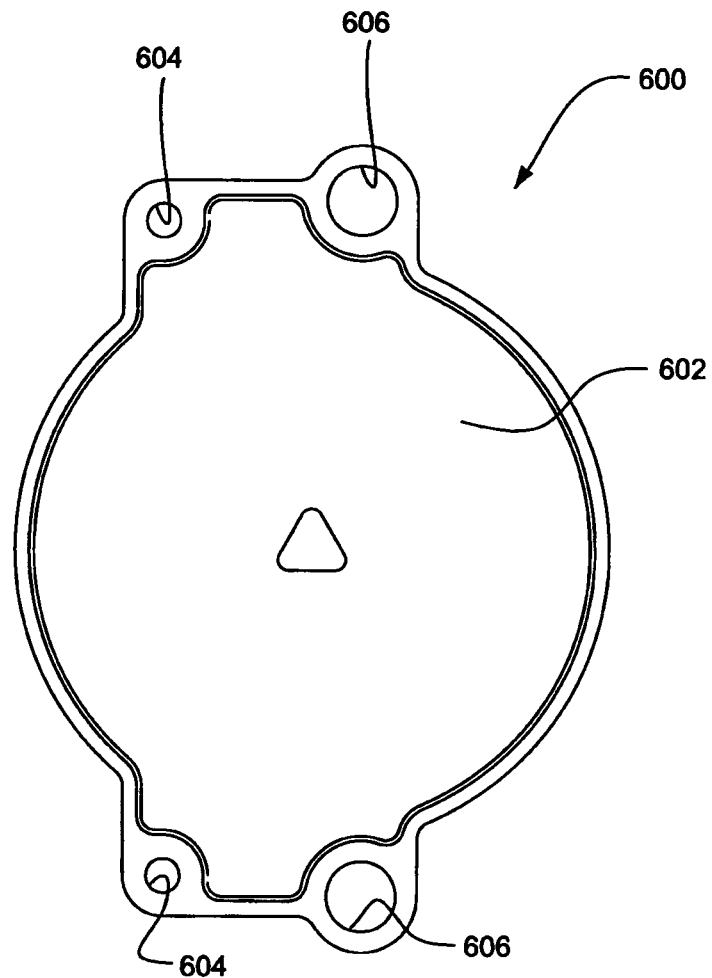
FIG. 22 is a top view of a blower bracket according to an example of the disclosed technology.
Figure 23:
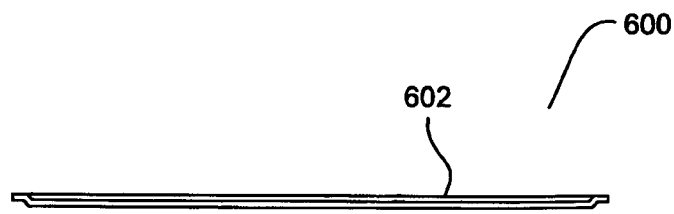
FIG. 23 is a side view of the blower bracket of FIG. 22.
Figure 24:
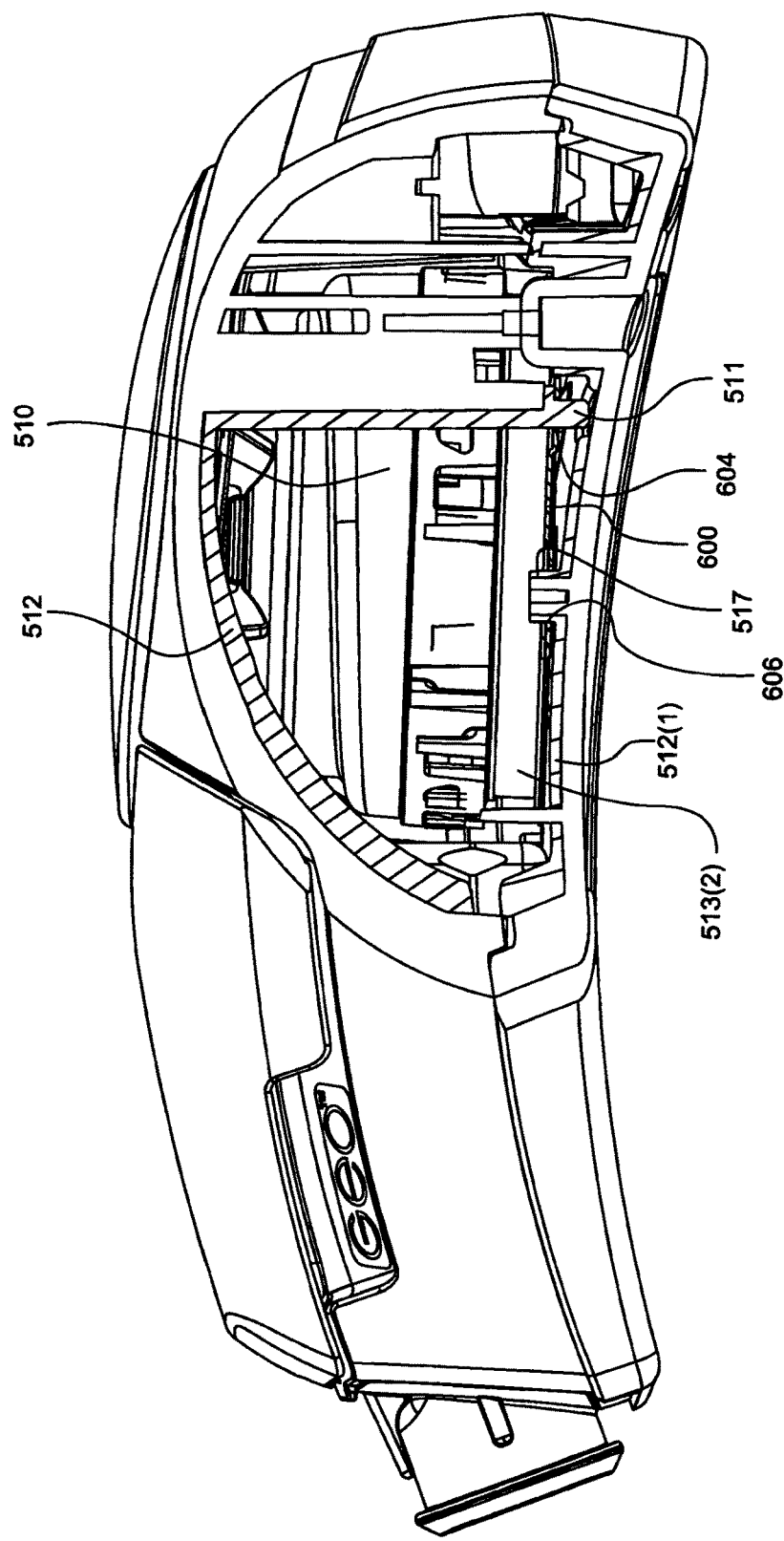
FIG. 24 is a cross-sectional view of the blower and blower bracket of FIG. 21 provided within the casing and cover.
Figure 25:
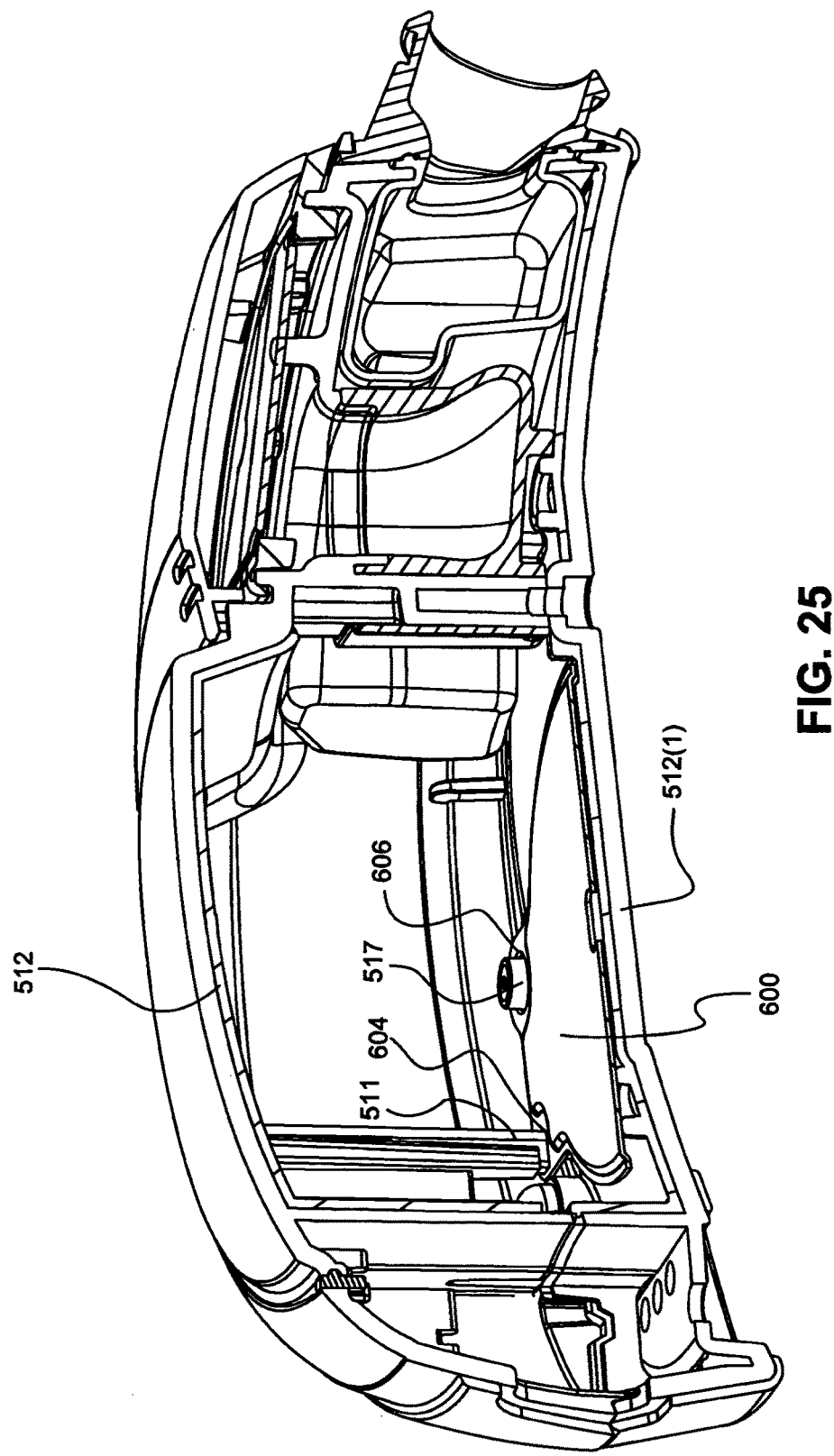
FIG. 25 is another cross-sectional view showing the blower bracket of FIG. 21 provided within the casing and cover.
Figure 26:
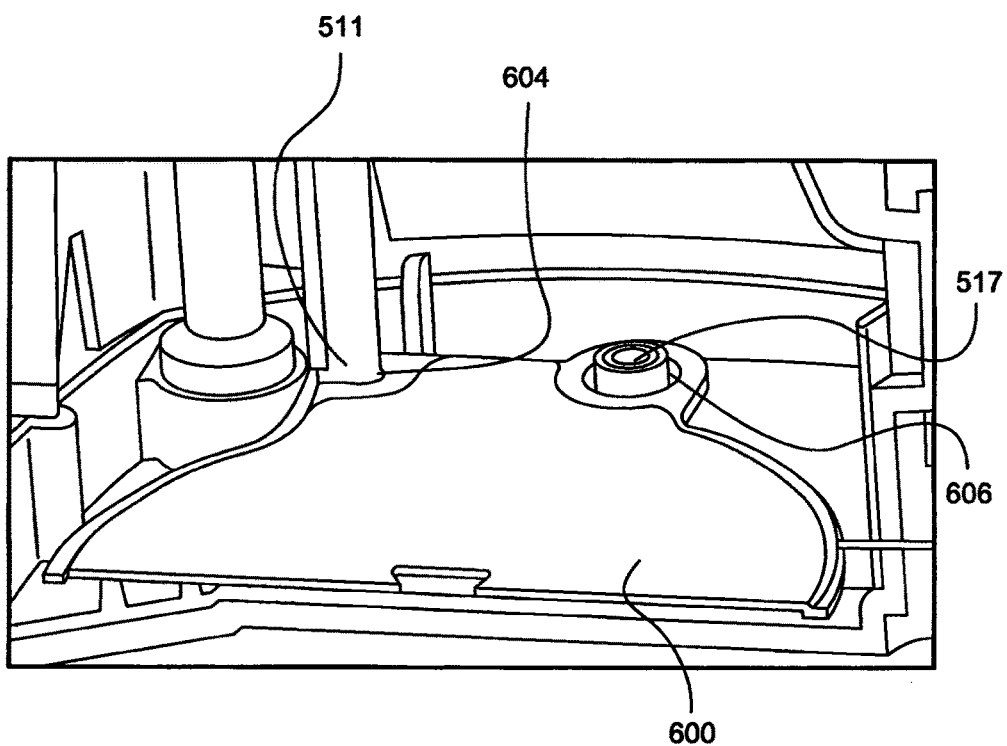
FIG. 26 is an enlarged cross-sectional view showing the blower bracket of FIG. 21 provided within the casing and cover.

As shown in FIG. 20 and further described in PCT Application No. PCT/US2010/003010, the blower 510 may be supported within a casing 512 of a PAP device including a removable cover or end wall (removable cover removed and not shown in FIG. 20). Insulators 513(1), 513(2) may be provided to respective ends of the blower to stably support the blower within the casing and absorb vibrations/noise (e.g., lower acoustic levels in both the narrow and ⅓ octave bands) from the blower in use.

In an alternative example, as shown in FIGS. 21 to 26, a blower bracket 600 may be provided to locate and align the blower 510 within the casing 512. As illustrated, the blower bracket 600 (e.g., a pressed part constructed for example from stainless steel, e.g., see FIG. 23) includes a main body 602 having a first pair of apertures 604 on opposite sides of the main body and a second pair of apertures 606 on opposite sides of the main body, the second pair of apertures 606 being larger than the first pair of apertures 604.

In use, the blower bracket 600 is attached to the base of the blower 510 and the apertures 604, 606 are adapted to receive respective alignment pins/bosses provided to the casing and cover. Specifically, the pair of smaller apertures 604 are adapted to receive respective alignment pins 511 provided to the casing 512 (e.g., see FIGS. 21 and 23-26), and the pair of larger apertures 606 are adapted to receive bosses 517 provided on the cover 512(1) (e.g., see FIGS. 24-26). The two alignment pins 511 (e.g., molded into the casing) align the blower bracket 600 and blower 510 within the casing 512, and the two bosses 517 (e.g., molded into the cover) assist in maintaining the blower in position, i.e., prevent movement of the blower within the casing in use. The blower bracket 600 may be sandwiched between the insulator 513(2) (e.g., constructed of foam) on the bottom of the blower and the removable cover (e.g., see FIG. 24).

The blower bracket allows for disassembly of the blower, e.g., if required for service. Optionally, the blower bracket may also perform the function of an EMF shield.

Figure 27:
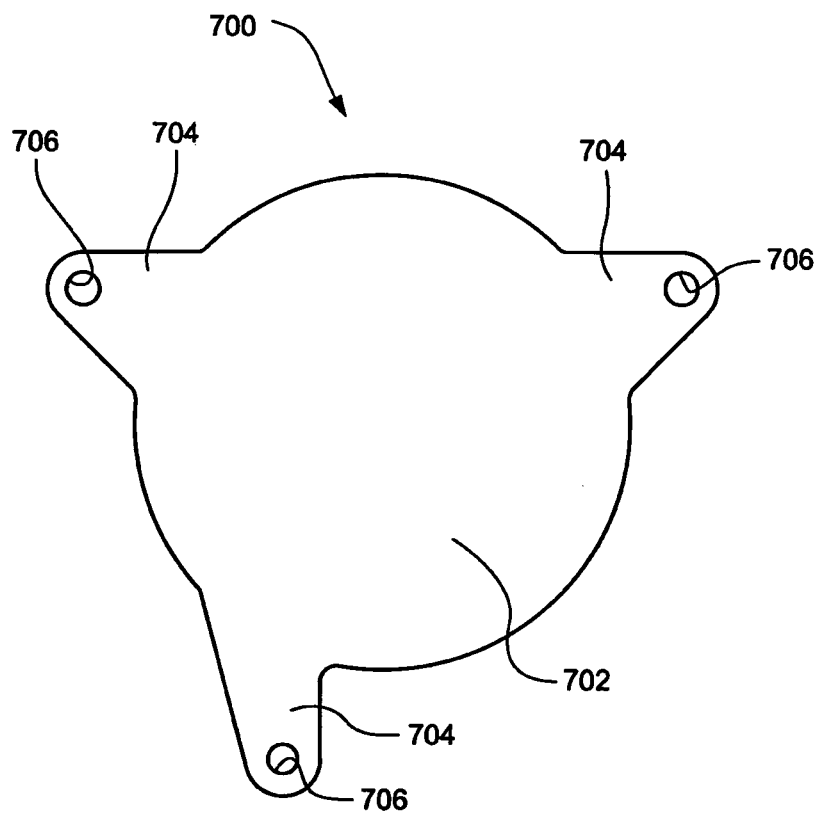
FIG. 27 is a top view of a blower bracket according to another example of the disclosed technology.
Figure 28:
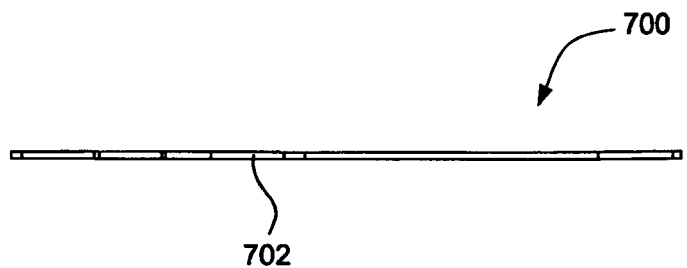
FIG. 28 is a side view of the blower bracket of FIG. 27.

In an alternative example, as shown in FIGS. 27 and 28, a blower bracket 700 may have a 3-legged design. As illustrated, the blower bracket 700 includes a main body 702 with three legs 704 each having an aperture 706 adapted to receive a respective alignment pin provided within the casing.

However, it should be appreciated that the blower bracket may have other suitable shapes to prevent movement of the blower within the casing in use.

Altitude Switch

Figure 30:
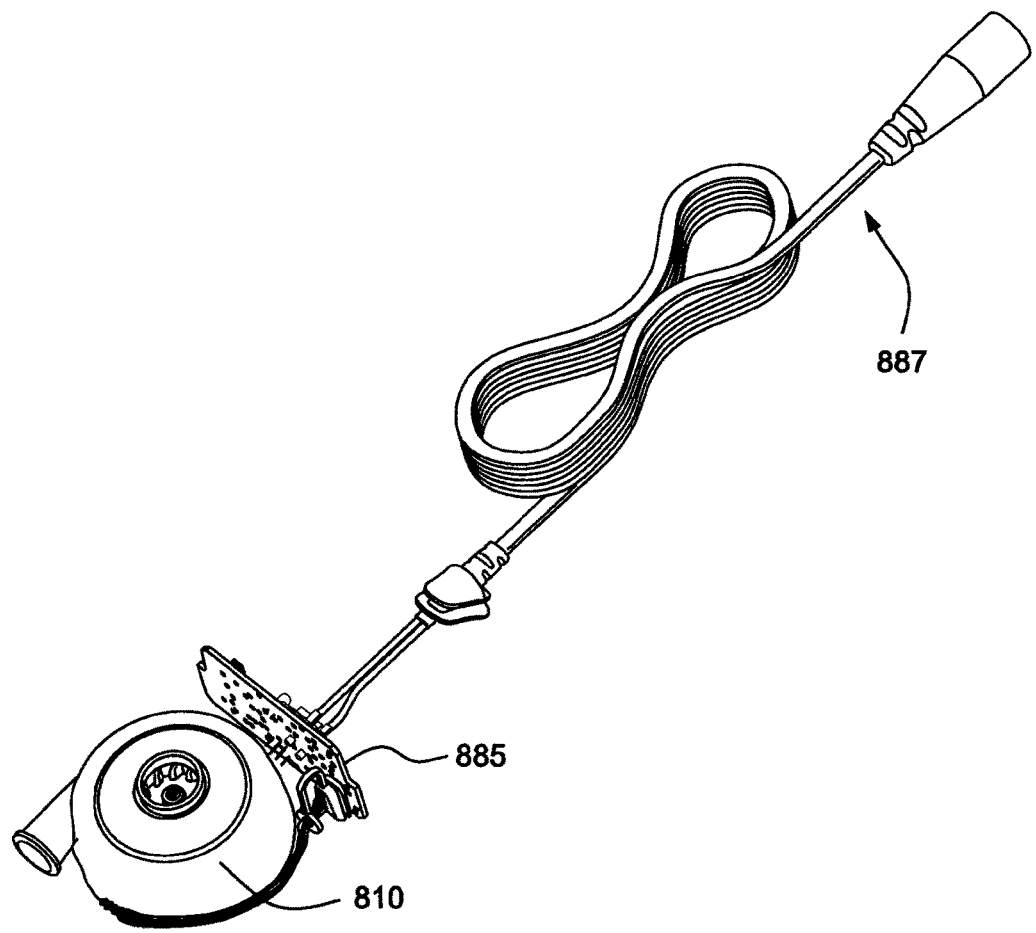
FIG. 30 is a perspective view of a blower and satellite PCBA according to an example of the disclosed technology.

As shown in FIG. 30 and further described in PCT Application No. PCT/US2010/003010, the PCBA within blower 810 may be coupled to a satellite PCBA 885, which satellite PCBA 885 is coupled to an overmolded power cord assembly 887. In an example, the satellite PCBA may include speed control and an altitude switch. The altitude switch may be used for travel purposes to update settings to compensate for changes in altitude. Also, the altitude switch may be manipulated by the patient, rather than the service provider.

Certain Examples Related to Noise Reduction

According to certain examples, the PAP system may be provided with an active noise cancellation system. According to other certain examples, the noise produced by the bearings of the flow generator, or blower, may be toned to produce a pleasant sound by using specific parameters of the bearings and controlling the harmonics. Additionally and/or alternatively, the speed of the blower may be varied to reduce the size of the noise peaks of the noise profile of the blower. The impeller blades of the blower may also be spaced unevenly around the impeller and/or the number of blades of the impeller may be increased to reduce the noise of the PAP system.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A blower, comprising:
   a housing including an inlet and an outlet;
   a stationary component provided to the housing, the stationary component comprising a tube portion;
   an impeller positioned between the inlet of the housing and the stationary component; and
   a motor adapted to drive the impeller,
   wherein the motor includes a rotor to which the impeller is coupled, the rotor including at least one retention groove configured to retain a blower component to the rotor in an operative position, and the rotor further including at least one annular groove configured to reduce a stiffness of the rotor, the at least one retention groove including a depth into the rotor that is smaller than a corresponding depth into the rotor of the at least one annular groove,
   wherein the tube portion includes an interior portion providing an interior surface structured to retain and align a pair of bearings that rotatably support the rotor, and the at least one annular groove is adapted to be positioned between the pair of bearings, and
   wherein the motor includes a magnet coupled to the rotor such that the magnet is arranged outside the interior portion.

2. The blower according to claim 1, wherein the at least one annular groove has a diameter of between about 2 mm and about 2.5 mm.

3. The blower according to claim 1, wherein the at least one annular groove has a width of between about 1 mm and about 2 mm.

4. The blower according to claim 1, wherein the at least one retention groove is arranged in a double helix configuration.

5. The blower according to claim 1,
   wherein the blower further comprises at least one of the following noise reduction features:
   (i) the tube portion includes a diameter in a side closest to the impeller that is sufficient size to accommodate adhesive to retain one of the pair of bearings;
   (ii) the stationary component and a stator assembly of the motor are overmolded with one another to provide a stationary assembly, the stationary assembly including a plurality of mounting protrusions to precisely position and align a printed circuit board assembly and its attendant components accurately with respect to the stationary assembly;
   (iii) a blower bracket to locate and align the blower within a casing; and/or
   (iv) a chimney or inlet tube portion provided to the inlet of the housing.

6. A PAP device adapted to provide a supply of pressurized breathable gas for treatment of a respiratory disease or sleep disordered breathing comprising:
   a casing; and
   the blower according to claim 1 supported within the casing.

7. The blower according to claim 1, wherein the at least one annular groove includes a diameter that extends transverse to a longitudinal axis of the rotor.

8. The blower according to claim 1, wherein the motor includes a stator assembly arranged outside the interior portion and arranged to interact with the magnet to control movement of the rotor.

9. The blower according to claim 1, wherein the blower component comprises the pair of bearings.

10. A flow generator adapted to provide a supply of pressurized breathable gas for treatment of a respiratory disease or sleep disordered breathing, comprising:
    a housing including an upper housing and a lower housing sealingly connected together, the upper housing including an air inlet opening;
    an inlet elbow supported within the housing between the upper housing and the lower housing, the inlet elbow arranged to be in fluid communication with the air inlet opening of the upper housing; and
    a blower comprising
      a blower housing including an inlet and an outlet;
      a stationary component provided to the blower housing;
      an impeller positioned between the inlet of the blower housing and the stationary component; and
      a motor adapted to drive the impeller, the motor including a rotor coupled to the impeller,
    wherein the inlet elbow is structured and arranged within the housing to direct incoming air flow from the air inlet opening of the upper housing to the lower housing for delivery to the blower, and
    wherein the inlet elbow is configured to reduce noise generated by the blower.

11. The flow generator according to claim 10, wherein the inlet elbow is curved to reflect sound wavelengths.

12. The flow generator according to claim 10, wherein the inlet elbow is formed of a flexible or elastomeric material.

13. The flow generator according to claim 12, wherein the inlet elbow is formed of silicone.

14. The flow generator according to claim 10, wherein the inlet of the blower is provided adjacent a top end of the upper housing and an outlet of the inlet elbow is provided adjacent a lower end of the lower housing.

15. The flow generator according to claim 10, wherein the inlet of the blower and an inlet of the inlet elbow are both oriented towards a top end of the upper housing.

16. The flow generator according to claim 10, wherein the inlet elbow includes a lower end that terminates above the lower housing with a gap.

17. The flow generator according to claim 10, wherein the air flow is dispersed into an internal area of the housing upon exiting a lower end of the inlet elbow.

18. The flow generator according to claim 17, wherein the inlet elbow disperses the air flow in 360° into the internal area.

19. The flow generator according to claim 10, wherein the inlet elbow provides a tubular conduit configured to direct air flow.

20. The flow generator according to claim 10, wherein the inlet elbow is configured to direct incoming air flow from the air inlet opening vertically downwards to the lower housing.

* * * * *